US010919959B2

(12) United States Patent
Chai et al.

(10) Patent No.: US 10,919,959 B2
(45) Date of Patent: Feb. 16, 2021

(54) ANGPTL3/8 COMPLEXES AND METHODS OF USING THE SAME

(71) Applicant: Eli Lilly and Company, Indianapolis, IN (US)

(72) Inventors: Qing Chai, San Diego, CA (US); Jonathan Wesley Day, Carmel, IN (US); Robert John Konrad, Carmel, IN (US); Yuewei Qian, Carmel, IN (US); Oliver Schroeder, Encinitas, CA (US); Robert William Siegel, Fountaintown, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/713,187

(22) Filed: Dec. 13, 2019

(65) Prior Publication Data

US 2020/0199212 A1    Jun. 25, 2020

Related U.S. Application Data

(60) Provisional application No. 62/783,260, filed on Dec. 21, 2018, provisional application No. 62/783,265, filed on Dec. 21, 2018.

(51) Int. Cl.
*C07K 16/22* (2006.01)
*A61P 3/00* (2006.01)
*A61K 39/00* (2006.01)

(52) U.S. Cl.
CPC .......... *C07K 16/22* (2013.01); *A61P 3/00* (2018.01); *A61K 2039/505* (2013.01); *C07K 2317/33* (2013.01); *C07K 2317/565* (2013.01); *C07K 2317/76* (2013.01); *C07K 2317/92* (2013.01)

(58) Field of Classification Search
CPC .......... C07K 16/22; C07K 2317/33; C07K 2317/565; C07K 2317/76; C07K 2317/92; A61P 3/00; A61K 2039/505
See application file for complete search history.

(56) References Cited

U.S. PATENT DOCUMENTS

| 7,935,796 B2 | 5/2011 | Lee et al. | |
|---|---|---|---|
| 2015/0197564 A1* | 7/2015 | Sleeman | A61K 31/455 424/139.1 |
| 2017/0143799 A1* | 5/2017 | Liu | A61P 3/06 |
| 2019/0060408 A1* | 2/2019 | Liu | A61K 38/22 |

FOREIGN PATENT DOCUMENTS

| WO | 2008/073300 A2 | 6/2008 |
|---|---|---|
| WO | 2011026000 A1 | 3/2011 |
| WO | 2012/174178 A1 | 12/2012 |
| WO | 2017/027316 A1 | 2/2017 |
| WO | 2017/177181 A1 | 10/2017 |
| WO | 2018/094112 A1 | 5/2018 |

OTHER PUBLICATIONS

Rishavy, MA and Berkner, KL. "Insight into the Coupling Mechanism of the Vitamin K-Dependent Carboxylase: Mutation of Histidine 160 Disrupts Glutamic Acid Carbanion Formation and Efficient Coupling of Vitamin K Epoxidation to Glutamic Acid Carboxylation". 2008. Biochemistry. 47, 9836-9846. (Year: 2008).*
Terpe, K. "Overview of tag protein fusions: from molecular and biochemical fundamentals to commercial system". 2003. Appl Microbiol Biotechnol. 60:523-533 (Year: 2003).*
"The Recombinant Protein Handbook". Amersham Pharmacia Biotech. [Online reference ] ][Aug. 2007 archived version downloaded from https://web.archive.org/web/20070824111423/http://wolfson.huji.ac.il/purification/PDF/Tag_Protein_Purification/AMERSHAM_TheRecombProtHandbook.pdf on Jun. 30, 2020] (Year: 2007).*
Liu, H. et al. "Enhanced production of secretory glycoprotein VSTM1-v2 with mouse IgGk signal peptide in optimized HEK293F transient transfection". Journal of Bioscience and Bioengineering vol. 121 No. 2, 133e139, 2016 (Year: 2016).*
Loonchanta, A. "Structural Studies of Gelsolin and Binding Partners". University of British Columbia, Vancouver, Aug. 2012; PhD thesis; p. 30 (Year: 2012).*
International Searching Authority, International Search Report for PCT/US2019/066151, Filed Dec. 13, 2019, dated Jun. 25, 2020.
International Searching Authority, Written Opinion for PCT/US2019/017925, filed Dec. 13, 2019, dated Jun. 25, 2020.
Chi, X., Britt, E. C., Shows, H. W., Hjelmaas, A. J., Shetty, S. K., Cushing, E. M., . . . & Davies, B. S. (2017). ANGPTL8 promotes the ability of ANGPTL3 to bind and inhibit lipoprotein lipase. *Molecular metabolism*, 6(10), 1137-1149.
Dewey, F. E., Gusarova, V., Dunbar, R. L., O'Dushlaine, C., Schurmann, C., Gottesman, O., . . . & Leader, J. B. (2017). Genetic and pharmacologic inactivation of ANGPTL3 and cardiovascular disease. *New England Journal of Medicine*, 377(3), 211-221.
Dewey, Frederick E., Viktoria Gusarova, Richard L. Dunbar, Colm O'Dushlaine, Claudia Schurmann, Omri Gottesman, Shane McCarthy et al. "Genetic and pharmacologic inactivation of ANGPTL3 and cardiovascular disease." *New England Journal of Medicine* 377, No. 3 (2017): 211-221.
Quagliarini, F., Wang, V., Kozlitina, J., Grishin, N. V., Hyde, R., Boerwinkle, E., . . . & Hobbs, H. H. (2012), Atypical angiopoietin-like protein that regulates ANGPTL3. *Proceedings of the National Academy of Sciences*, 109(48), 19751-19756.

* cited by examiner

*Primary Examiner* — Joanne Hama
*Assistant Examiner* — Scott T. Humbarger
(74) *Attorney, Agent, or Firm* — Brian C Cholewa

(57) ABSTRACT

Angiopoietin-like protein (ANGPTL)3/8 complexes and antibodies are disclosed, where the antibodes bind to and thereby neutralize ANGPTL3/8 complexes. Pharmaceutical compositions also are disclosed that include one or more anti-ANGPTL3/8 complex antibodies herein in a pharmaceutically acceptable carrier. Methods of making and using the same also are disclosed, especially for increase lipoprotein lipase activity and lowering triglycerides. In this manner, the compounds and compositions may be used in treating lipid metabolism-related and glucose metabolism-related diseases and disorders.

2 Claims, 1 Drawing Sheet

Specification includes a Sequence Listing.

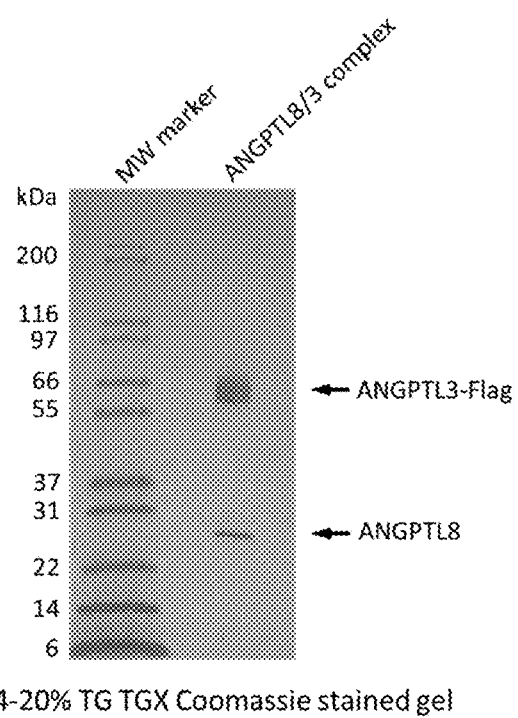

SEQUENCE LISTING

<160> NUMBER OF SEQ ID NOS: 25

<210> SEQ ID NO 1
<211> LENGTH: 2951
<212> TYPE: DNA
<213> ORGANISM: Homo sapiens

<400> SEQUENCE: 1

```
atatatagag ttaagaagtc taggtctgct tccagaagaa aacagttcca cgttgcttga     60
aattgaaaat caagataaaa atgttcacaa ttaagctcct tcttttttatt gttcctctag    120 ttatttcctc cagaattgat caagacaatt catcatttga ttctctatct ccagagccaa    180
aatcaagatt tgctatgtta gacgatgtaa aaatttttagc caatggcctc cttcagttgg    240
```

```
gacatggtct taaagacttt gtccataaga cgaagggcca aattaatgac atatttcaaa    300
aactcaacat atttgatcag tcttttttatg atctatcgct gcaaaccagt gaaatcaaag    360
aagaagaaaa ggaactgaga agaactacat ataaactaca agtcaaaaat gaagaggtaa    420
agaatatgtc acttgaactc aactcaaaac ttgaaagcct cctagaagaa aaaattctac    480
ttcaacaaaa agtgaaatat ttagaagagc aactaactaa cttaattcaa aatcaacctg    540
aaactccaga acacccagaa gtaacttcac ttaaaacttt tgtagaaaaa caagataata    600
gcatcaaaga ccttctccag accgtggaag accaatataa acaattaaac caacagcata    660
gtcaaataaa agaaatagaa atcagctcga aaggactag tattcaagaa cccacagaaa    720
tttctctatc ttccaagcca agagcaccaa gaactactcc ctttcttcag ttgaatgaaa    780
taagaaatgt aaaacatgat ggcattcctg ctgaatgtac caccattat aacagaggtg    840 aacatacaag tggcatgtat gccatcagac ccagcaactc tcaagttttt catgtctact    900
gtgatgttat atcaggtagt ccatggacat taattcaaca tcgaatagat ggatcacaaa    960
acttcaatga aacgtgggag aactacaaat atggttttgg gaggcttgat ggagaatttt   1020
ggttgggcct agagaagata tactccatag tgaagcaatc taattatgtt ttacgaattg   1080
agttggaaga ctgaaagac aacaaacatt atattgaata ttcttttac ttgggaaatc   1140 acgaaaccaa ctatacgcta catctagttg cgattactgg caatgtcccc aatgcaatcc   1200
cggaaaacaa agatttggtg ttttctactt gggatcacaa agcaaaagga cacttcaact   1260
gtccagaggg ttattcagga ggctggtggt ggcatgatga gtgtggagaa acaacctaa   1320 atggtaaata taacaaacca agagcaaaat ctaagccaga gaggagaaga ggattatctt   1380
ggaagtctca aaatggaagg ttatactcta aaaatcaac caaatgttg atccatccaa   1440 cagattcaga aagctttgaa tgaactgagg caaatttaaa aggcaataat ttaaacatta   1500
acctcattcc aagttaatgt ggtctaataa tctggtatta aatccttaag agaaagcttg   1560
agaaatagat tttttttatc ttaaagtcac tgtctattta agattaaaca tacaatcaca   1620
taaccttaaa gaataccgtt tacatttctc aatcaaaatt cttataatac tatttgtttt   1680
aaattttgtg atgtgggaat caattttaga tggtcacaat ctagattata atcaataggt   1740
gaacttatta ataacttttt ctaaataaaa aatttagaga cttttatttt aaaaggcatc   1800
atatgagcta atatcacaac tttcccagtt taaaaaacta gtactcttgt taaaactcta   1860
aacttgacta aatacagagg actggtaatt gtacagttct taaatgttgt agtattaatt   1920
tcaaaactaa aaatcgtcag cacagagtat gtgtaaaaat ctgtaataca aatttttaaa   1980
ctgatgcttc attttgctac aaaataattt ggagtaaatg tttgatatga tttatttatg   2040
aaacctaatg aagcagaatt aaatactgta ttaaaataag ttcgctgtct ttaaacaaat   2100
ggagatgact actaagtcac attgacttta acatgaggta tcactatacc ttatttgtta   2160
aaatatatac tgtatacatt ttatatattt taacacttaa tactatgaaa acaaataatt   2220
gtaaaggaat cttgtcagat tacagtaaga atgaacatat ttgtggcatc gagttaaagt   2280
ttatatttcc cctaaatatg ctgtgattct aatacattcg tgtaggtttt caagtagaaa   2340
taaacctcgt aacaagttac tgaacgttta aacagcctga caagcatgta tatatgttta   2400
aaattcaata aacaaagacc cagtccctaa attatagaaa tttaaattat tcttgcatgt   2460
ttatcgacat cacaacagat ccctaaatcc ctaaatccct aaagattaga tacaaatttt   2520
ttaccacagt atcacttgtc agaatttatt tttaaatatg attttttaaa actgccagta   2580
agaaatttta aattaaaccc atttgttaaa ggatatagtg cccaagttat atggtgacct   2640
```

```
accctttgtca atacttagca ttatgtattt caaattatcc aatatacatg tcatatatat    2700
ttttatatgt cacatatata aaagatatgt atgatctatg tgaatcctaa gtaaatattt    2760
tgttccagaa aagtacaaaa taataaaggt aaaaataatc tataatttc aggaccacag     2820 actaagctgt cgaaattaac gctgattttt ttagggccag aataccaaaa tggctcctct    2880
cttcccccaa aattggacaa tttcaaatgc aaaataattc attatttaat atatgagttg    2940
cttcctctat t                                                         2951
```

<210> SEQ ID NO 2
<211> LENGTH: 460
<212> TYPE: PRT
<213> ORGANISM: Homo sapiens

<400> SEQUENCE: 2

```
Met Phe Thr Ile Lys Leu Leu Leu Phe Ile Val Pro Leu Val Ile Ser
 1               5                  10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320
```

```
Tyr Ser Ile Val Lys Gln Ser Asn Tyr Val Leu Arg Ile Glu Leu Glu
            325                 330                 335

Asp Trp Lys Asp Asn Lys His Tyr Ile Glu Tyr Ser Phe Tyr Leu Gly
        340                 345                 350

Asn His Glu Thr Asn Tyr Thr Leu His Leu Val Ala Ile Thr Gly Asn
            355                 360                 365

Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
    450                 455                 460

<210> SEQ ID NO 3
<211> LENGTH: 888
<212> TYPE: DNA
<213> ORGANISM: Homo sapiens

<400> SEQUENCE: 3
ataccttaga ccctcagtca tgccagtgcc tgctctgtgc ctgctctggg ccctggcaat      60
ggtgacccgg cctgcctcag cggcccccat gggcggccca gaactggcac agcatgagga    120
gctgaccctg ctcttccatg gaccctgca gctgggccag ccctcaacg tgtgtacag       180
gaccacggag ggacggctga caaaggccag gaacagcctg gtctctatg ccgcacaat      240
agaactcctg gggcaggagg tcagccgggg ccgggatgca gcccaggaac ttcgggcaag    300
cctgttggag actcagatgg aggaggatat tctgcagctg caggcagagg ccacagctga    360
ggtgctgggg gaggtggccc aggcacagaa ggtgctacgg gacagcgtgc agcggctaga    420
agtccagctg aggagcgcct ggctgggccc tgcctaccga gaatttgagg tcttaaaggc    480
tcacgctgac aagcagagcc acatcctatg ggccctcaca ggccacgtgc agcggcagag    540
gcgggagatg gtggcacagc agcatcggct gcgacagatc caggagagac tccacacagc    600
ggcgctccca gcctgaatct gcctggatgg aactgaggac caatcatgct gcaaggaaca    660
cttccacgcc ccgtgaggcc cctgtgcagg gaggagctgc ctgttcactg ggatcagcca    720
gggcgccggg ccccacttct gagcacagag cagagacaga cgcaggcggg gacaaaggca    780
gaggatgtag ccccattggg gagggtgga ggaaggacat gtacccttc atgcctacac      840
accctcatt aaagcagagt cgtggcatct caaaaaaaaa aaaaaaaa                  888

<210> SEQ ID NO 4
<211> LENGTH: 198
<212> TYPE: PRT
<213> ORGANISM: Homo sapiens

<400> SEQUENCE: 4

Met Pro Val Pro Ala Leu Cys Leu Leu Trp Ala Leu Ala Met Val Thr
1               5                   10                  15

Arg Pro Ala Ser Ala Ala Pro Met Gly Gly Pro Glu Leu Ala Gln His
            20                  25                  30
```

Glu Glu Leu Thr Leu Phe His Gly Thr Leu Gln Leu Gly Gln Ala
            35                  40                  45

Leu Asn Gly Val Tyr Arg Thr Glu Gly Arg Leu Thr Lys Ala Arg
 50                  55                  60

Asn Ser Leu Gly Leu Tyr Gly Arg Thr Ile Glu Leu Leu Gly Gln Glu
65                  70                  75                  80

Val Ser Arg Gly Arg Asp Ala Ala Gln Glu Leu Arg Ala Ser Leu Leu
                85                  90                  95

Glu Thr Gln Met Glu Glu Asp Ile Leu Gln Leu Gln Ala Glu Ala Thr
                100                 105                 110

Ala Glu Val Leu Gly Glu Val Ala Gln Ala Gln Lys Val Leu Arg Asp
            115                 120                 125

Ser Val Gln Arg Leu Glu Val Gln Leu Arg Ser Ala Trp Leu Gly Pro
    130                 135                 140

Ala Tyr Arg Glu Phe Glu Val Leu Lys Ala His Ala Asp Lys Gln Ser
145                 150                 155                 160

His Ile Leu Trp Ala Leu Thr Gly His Val Gln Arg Gln Arg Arg Glu
                165                 170                 175

Met Val Ala Gln Gln His Arg Leu Arg Gln Ile Gln Glu Arg Leu His
            180                 185                 190

Thr Ala Ala Leu Pro Ala
            195

<210> SEQ ID NO 5
<211> LENGTH: 220
<212> TYPE: PRT
<213> ORGANISM: Artificial Sequence
<220> FEATURE:
<223> OTHER INFORMATION: Synthetic Construct

<400> SEQUENCE: 5

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Met Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met Gln
                85                  90                  95

Arg Ile Glu Phe Pro Leu Thr Phe Gly Gly Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 6
<211> LENGTH: 449
<212> TYPE: PRT
<213> ORGANISM: Artificial Sequence
<220> FEATURE:
<223> OTHER INFORMATION: Synthetic Construct

<400> SEQUENCE: 6

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Ile Ser
            20                  25                  30

Gly Val Gly Val Gly Trp Ile Arg Gln Pro Pro Gly Lys Ala Leu Glu
        35                  40                  45

Trp Leu Ala Leu Ile Tyr Arg Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Leu Thr Asn Met Asp Pro Val Asp Thr Ala Thr Tyr Tyr
                85                  90                  95

Cys Ala Arg Thr Tyr Ser Ser Gly Trp Tyr Gly Asn Trp Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

| | | | | | | | | | | | |
|---|---|---|---|---|---|---|---|---|---|---|---|
|Lys|Thr|Ile|Ser|Lys|Ala|Lys|Gly|Gln|Pro|Arg|Glu|Pro|Gln|Val|Tyr|
| | | |340| | | |345| | | |350| | | | |

| | | | | | | | | | | | | | | |
|---|---|---|---|---|---|---|---|---|---|---|---|---|---|---|
|Thr|Leu|Pro|Pro|Ser|Gln|Glu|Glu|Met|Thr|Lys|Asn|Gln|Val|Ser|Leu|
| | |355| | | | |360| | | | |365| | | |

| | | | | | | | | | | | | | | |
|---|---|---|---|---|---|---|---|---|---|---|---|---|---|---|
|Thr|Cys|Leu|Val|Lys|Gly|Phe|Tyr|Pro|Ser|Asp|Ile|Ala|Val|Glu|Trp|
| |370| | | | |375| | | | |380| | | | |

| | | | | | | | | | | | | | | |
|---|---|---|---|---|---|---|---|---|---|---|---|---|---|---|
|Glu|Ser|Asn|Gly|Gln|Pro|Glu|Asn|Asn|Tyr|Lys|Thr|Thr|Pro|Pro|Val|
|385| | | |390| | | | |395| | | | |400| |

| | | | | | | | | | | | | | | |
|---|---|---|---|---|---|---|---|---|---|---|---|---|---|---|
|Leu|Asp|Ser|Asp|Gly|Ser|Phe|Phe|Leu|Tyr|Ser|Arg|Leu|Thr|Val|Asp|
| | | | |405| | | | |410| | | | |415| |

| | | | | | | | | | | | | | | |
|---|---|---|---|---|---|---|---|---|---|---|---|---|---|---|
|Lys|Ser|Arg|Trp|Gln|Glu|Gly|Asn|Val|Phe|Ser|Cys|Ser|Val|Met|His|
| | |420| | | | |425| | | | |430| | | |

| | | | | | | | | | | | | | | |
|---|---|---|---|---|---|---|---|---|---|---|---|---|---|---|
|Glu|Ala|Leu|His|Asn|His|Tyr|Thr|Gln|Lys|Ser|Leu|Ser|Leu|Ser|Leu|
| | |435| | | |440| | | | |445| | | | |

Gly

```
<210> SEQ ID NO 7
<211> LENGTH: 660
<212> TYPE: DNA
<213> ORGANISM: Artificial Sequence
<220> FEATURE:
<223> OTHER INFORMATION: Synthetic Construct

<400> SEQUENCE: 7
gatattgtga tgacccagac cccctgtct ctgcctgtca ctccggggga accggcctcg     60
atctcatgcc ggtcgagcca gtccctgctg gactccgatg acgggaacac ttatttggat    120
tggtacctcc aaaagcctgg acagagcccg cagtcctga tctacatgct gtcctaccgg    180
gcctccggag tgccagaccg cttctcggga agcggctccg gtaccgactt cacactgaag    240
atctcccgcg tggaagctga ggacgtgggc atctactact gtatgcaaag aatcgagttc    300
cccctcacct tcggcggcgg gactaaggtc gagattaaga gaaccgtggc cgcaccatcc    360
gtgttcattt ttcccccgtc cgatgaacag ctgaagtccg gaaccgcctc cgtcgtgtgc    420
ctgctcaaca acttctaccc gagggaagcg aaagtgcagt ggaaagtgga caatgcgctg    480
cagtccggaa actcccaaga gtccgtgacc gaacaggact ccaaggactc aacctactcg    540
ctgagctcaa cgctgaccct gagcaaggcc gactacgaga agcacaaggt ctacgcctgc    600
gaagtgaccc atcagggttt gagctcgccc gtgaccaagt ccttcaaccg gggagagtgc    660

<210> SEQ ID NO 8
<211> LENGTH: 1347
<212> TYPE: DNA
<213> ORGANISM: Artificial Sequence
<220> FEATURE:
<223> OTHER INFORMATION: Synthetic Construct

<400> SEQUENCE: 8
caagtcacat tgaaggagag cggtccgacc ctggtcaagc cgactcagac cctgaccctg     60
acgtgcactt tctcgggctt ctcattgtcc atttctggag tgggcgtggg atggatcaga    120
cagcccccgg ggaaggccct cgagtggctc gcgctgatct accgcaacga cgacaaacgc    180
tactccccct cactgaaatc ccggctgacc atcactaagg atacgtccaa gaaccaggtc    240
gtgttgaccc tcaccaacat ggatcccgtg gatactgcca cctactattg tgcacggacc    300
tatagcagcg gttggtacgg aaactggttc gacccgtggg gccagggaac tcttgtgacg    360
gtgtcctccg caagcaccaa gggtccttct gtgttccccc tggcgccgtg ctcgcggagc    420
```

| | | |
|---|---|---|
| acctcagagt ccaccgccgc cctcggctgc cttgtgaagg actacttccc ggagccagtc | 480 | |
| accgtgtcct ggaacagcgg ggccctgact ccggcgtgc acaccttccc tgcggtgctg | 540 | |
| cagagctcag gcctctattc gctgtcatcc gtcgtgaccg tgccttcctc gtccctgggc | 600 | |
| actaagacct acacttgcaa cgtggaccat aagcccagca acaccaaagt ggacaagaga | 660 | |
| gtggaatcca atacggacc gccatgtccg ccctgcccg ccccggaagc tgccggggga | 720 | |
| cccagcgtgt tcctgttccc acctaagccg aaggacactc tgatgatctc aaggactccc | 780 | |
| gaagtcactt gcgtggtcgt ggacgtgtcc caggaggacc ccgaagtcca gtttaattgg | 840 | |
| tacgtggatg gtgtcgaggt ccacaacgcc aagaccaagc ctcgcgagga acagttcaat | 900 | |
| tccacctacc gggtcgtgtc cgtcctgacc gtgctgcatc aggactggct gaacggaaag | 960 | |
| gagtacaagt gcaaagtgtc caacaaggga ctcccttcct ccatcgaaaa gaccatcagc | 1020 | |
| aaggccaagg gccagcctcg cgaaccacaa gtctacaccc tgcccccatc gcaagaggaa | 1080 | |
| atgaccaaga accaagtgtc gctgacatgc ctcgtcaagg gattctaccc gtcggatatt | 1140 | |
| gcggtggaat gggagtccaa cggacagccc gagaacaact acaagaccac cccgccggtg | 1200 | |
| ttggactccg acggctcctt tttcctgtac tcccggctca ctgtggacaa gtcgcggtgg | 1260 | |
| caggagggga acgtgttctc ctgttccgtg atgcacgaag ctctgcacaa ccactacacc | 1320 | |
| cagaagtcgc tgagcctctc actggga | 1347 | |

<210> SEQ ID NO 9
<211> LENGTH: 113
<212> TYPE: PRT
<213> ORGANISM: Artificial Sequence
<220> FEATURE:
<223> OTHER INFORMATION: Synthetic Construct

<400> SEQUENCE: 9

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Met Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met Gln
                85                  90                  95

Arg Ile Glu Phe Pro Leu Thr Phe Gly Gly Gly Thr Lys Val Glu Ile
            100                 105                 110

Lys

<210> SEQ ID NO 10
<211> LENGTH: 123
<212> TYPE: PRT
<213> ORGANISM: Artificial Sequence
<220> FEATURE:
<223> OTHER INFORMATION: Synthetic Construct

```
<400> SEQUENCE: 10

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Ile Ser
            20                  25                  30

Gly Val Gly Val Gly Trp Ile Arg Gln Pro Pro Gly Lys Ala Leu Glu
        35                  40                  45

Trp Leu Ala Leu Ile Tyr Arg Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Leu Thr Asn Met Asp Pro Val Asp Thr Ala Thr Tyr Tyr
                85                  90                  95

Cys Ala Arg Thr Tyr Ser Ser Gly Trp Tyr Gly Asn Trp Phe Asp Pro
            100                 105                 110

Trp Gly Gln Gly Thr Leu Val Thr Val Ser Ser
        115                 120

<210> SEQ ID NO 11
<211> LENGTH: 17
<212> TYPE: PRT
<213> ORGANISM: Artificial Sequence
<220> FEATURE:
<223> OTHER INFORMATION: Synthetic Construct

<400> SEQUENCE: 11

Arg Ser Ser Gln Ser Leu Leu Asp Ser Asp Gly Asn Thr Tyr Leu
1               5                   10                  15

Asp

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct

<400> SEQUENCE: 12

Tyr Met Leu Ser Tyr Arg Ala Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Met Gln Arg Ile Glu Phe Pro Leu Thr
1               5

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Thr Phe Ser Gly Phe Ser Leu Ser Ile Ser Gly Val Gly Val Gly
1               5                   10                  15
```

```
<210> SEQ ID NO 15
<211> LENGTH: 16
<212> TYPE: PRT
<213> ORGANISM: Artificial Sequence
<220> FEATURE:
<223> OTHER INFORMATION: Synthetic Construct

<400> SEQUENCE: 15

Leu Ile Tyr Arg Asn Asp Asp Lys Arg Tyr Ser Pro Ser Leu Lys Ser
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic Construct

<400> SEQUENCE: 16

Ala Arg Thr Tyr Ser Ser Gly Trp Tyr Gly Asn Trp Phe Asp Pro
1               5                   10                  15

<210> SEQ ID NO 17
<211> LENGTH: 471
<212> TYPE: PRT
<213> ORGANISM: Artificial Sequence
<220> FEATURE:
<223> OTHER INFORMATION: Synthetic Construct

<400> SEQUENCE: 17

Met Phe Thr Ile Lys Leu Leu Phe Ile Val Pro Leu Val Ile Ser
1               5                   10                  15

Ser Arg Ile Asp Gln Asp Asn Ser Ser Phe Asp Ser Leu Ser Pro Glu
                20                  25                  30

Pro Lys Ser Arg Phe Ala Met Leu Asp Asp Val Lys Ile Leu Ala Asn
            35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
    115                 120                 125

Glu Glu Lys Ile Leu Leu Gln Gln Lys Val Lys Tyr Leu Glu Glu Gln
130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
    195                 200                 205

Gln Glu Pro Thr Glu Ile Ser Leu Ser Ser Lys Pro Arg Ala Pro Arg
210                 215                 220

Thr Thr Pro Phe Leu Gln Leu Asn Glu Ile Arg Asn Val Lys His Asp
225                 230                 235                 240
```

-continued

```
Gly Ile Pro Ala Glu Cys Thr Thr Ile Tyr Asn Arg Gly Glu His Thr
            245                 250                 255

Ser Gly Met Tyr Ala Ile Arg Pro Ser Asn Ser Gln Val Phe His Val
        260                 265                 270

Tyr Cys Asp Val Ile Ser Gly Ser Pro Trp Thr Leu Ile Gln His Arg
    275                 280                 285

Ile Asp Gly Ser Gln Asn Phe Asn Glu Thr Trp Glu Asn Tyr Lys Tyr
290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu Ala Ala Ala Asp
    450                 455                 460

Tyr Lys Asp Asp Asp Asp Lys
465                 470

<210> SEQ ID NO 18
<211> LENGTH: 820
<212> TYPE: PRT
<213> ORGANISM: Artificial Sequence
<220> FEATURE:
<223> OTHER INFORMATION: Synthetic Construct

<400> SEQUENCE: 18

Met Glu Thr Asp Thr Leu Leu Leu Trp Val Leu Leu Leu Trp Val Pro
1               5                   10                  15

Gly Ser Thr Gly Asp His His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Ser Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125
```

```
Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
        355                 360                 365

Ser Val Val Leu Leu Leu Arg Leu Ala Lys Thr Tyr Glu Thr Thr Leu
    370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
            420                 425                 430

Ala Leu Leu Val Arg Tyr Thr Lys Lys Val Pro Gln Val Ser Thr Pro
        435                 440                 445

Thr Leu Val Glu Val Ser Arg Asn Leu Gly Lys Val Gly Ser Lys Cys
    450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
            500                 505                 510

Pro Cys Phe Ser Ala Leu Glu Val Asp Glu Thr Tyr Val Pro Lys Glu
        515                 520                 525

Phe Asn Ala Glu Thr Phe Thr Phe His Ala Asp Ile Cys Thr Leu Ser
    530                 535                 540
```

```
Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
            565                 570                 575

Asp Phe Ala Ala Phe Val Glu Lys Cys Cys Lys Ala Asp Asp Lys Glu
                580                 585                 590

Thr Cys Phe Ala Glu Glu Gly Lys Lys Leu Val Ala Ala Ser Gln Ala
            595                 600                 605

Ala Leu Gly Leu Ala Pro Pro Ala Pro Ala Pro Ala Pro Ala Pro Ala
        610                 615                 620

Ala Pro Ala Pro Ala Pro Ala Pro Leu Glu Val Leu Phe Gln Gly Pro
625                 630                 635                 640

Gly Arg Ala Ala Pro Met Gly Gly Pro Glu Leu Ala Gln His Glu Glu
                645                 650                 655

Leu Thr Leu Leu Phe His Gly Thr Leu Gln Leu Gly Gln Ala Leu Asn
            660                 665                 670

Gly Val Tyr Arg Thr Thr Glu Gly Arg Leu Thr Lys Ala Arg Asn Ser
        675                 680                 685

Leu Gly Leu Tyr Gly Arg Thr Ile Glu Leu Leu Gly Gln Glu Val Ser
690                 695                 700

Arg Gly Arg Asp Ala Ala Gln Glu Leu Arg Ala Ser Leu Leu Glu Thr
705                 710                 715                 720

Gln Met Glu Glu Asp Ile Leu Gln Leu Gln Ala Glu Ala Thr Ala Glu
                725                 730                 735

Val Leu Gly Glu Val Ala Gln Ala Gln Lys Val Leu Arg Asp Ser Val
            740                 745                 750

Gln Arg Leu Glu Val Gln Leu Arg Ser Ala Trp Leu Gly Pro Ala Tyr
        755                 760                 765

Arg Glu Phe Glu Val Leu Lys Ala His Ala Asp Lys Gln Ser His Ile
770                 775                 780

Leu Trp Ala Leu Thr Gly His Val Gln Arg Gln Arg Arg Glu Met Val
785                 790                 795                 800

Ala Gln Gln His Arg Leu Arg Gln Ile Gln Glu Arg Leu His Thr Ala
                805                 810                 815

Ala Leu Pro Ala
            820

<210> SEQ ID NO 19
<211> LENGTH: 455
<212> TYPE: PRT
<213> ORGANISM: Artificial Sequence
<220> FEATURE:
<223> OTHER INFORMATION: Synthetic Construct

<400> SEQUENCE: 19

Ser Arg Ile Asp Gln Asp Asn Ser Ser Phe Asp Ser Leu Ser Pro Glu
1               5                   10                  15

Pro Lys Ser Arg Phe Ala Met Leu Asp Asp Val Lys Ile Leu Ala Asn
                20                  25                  30

Gly Leu Leu Gln Leu Gly His Gly Leu Lys Asp Phe Val His Lys Thr
            35                  40                  45

Lys Gly Gln Ile Asn Asp Ile Phe Gln Lys Leu Asn Ile Phe Asp Gln
        50                  55                  60

Ser Phe Tyr Asp Leu Ser Leu Gln Thr Ser Glu Ile Lys Glu Glu Glu
65                  70                  75                  80
```

Lys Glu Leu Arg Arg Thr Thr Tyr Lys Leu Gln Val Lys Asn Glu Glu
            85                  90                  95

Val Lys Asn Met Ser Leu Glu Leu Asn Ser Lys Leu Glu Ser Leu Leu
        100                 105                 110

Glu Glu Lys Ile Leu Leu Gln Gln Lys Val Lys Tyr Leu Glu Glu Gln
        115                 120                 125

Leu Thr Asn Leu Ile Gln Asn Gln Pro Glu Thr Pro Glu His Pro Glu
        130                 135                 140

Val Thr Ser Leu Lys Thr Phe Val Glu Lys Gln Asp Asn Ser Ile Lys
145                 150                 155                 160

Asp Leu Leu Gln Thr Val Glu Asp Gln Tyr Lys Gln Leu Asn Gln Gln
                165                 170                 175

His Ser Gln Ile Lys Glu Ile Glu Asn Gln Leu Arg Arg Thr Ser Ile
                180                 185                 190

Gln Glu Pro Thr Glu Ile Ser Leu Ser Ser Lys Pro Arg Ala Pro Arg
        195                 200                 205

Thr Thr Pro Phe Leu Gln Leu Asn Glu Ile Arg Asn Val Lys His Asp
        210                 215                 220

Gly Ile Pro Ala Glu Cys Thr Thr Ile Tyr Asn Arg Gly Glu His Thr
225                 230                 235                 240

Ser Gly Met Tyr Ala Ile Arg Pro Ser Asn Ser Gln Val Phe His Val
                245                 250                 255

Tyr Cys Asp Val Ile Ser Gly Ser Pro Trp Thr Leu Ile Gln His Arg
                260                 265                 270

Ile Asp Gly Ser Gln Asn Phe Asn Glu Thr Trp Glu Asn Tyr Lys Tyr
        275                 280                 285

Gly Phe Gly Arg Leu Asp Gly Glu Phe Trp Leu Gly Leu Glu Lys Ile
        290                 295                 300

Tyr Ser Ile Val Lys Gln Ser Asn Tyr Val Leu Arg Ile Glu Leu Glu
305                 310                 315                 320

Asp Trp Lys Asp Asn Lys His Tyr Ile Glu Tyr Ser Phe Tyr Leu Gly
                325                 330                 335

Asn His Glu Thr Asn Tyr Thr Leu His Leu Val Ala Ile Thr Gly Asn
                340                 345                 350

Val Pro Asn Ala Ile Pro Glu Asn Lys Asp Leu Val Phe Ser Thr Trp
        355                 360                 365

Asp His Lys Ala Lys Gly His Phe Asn Cys Pro Glu Gly Tyr Ser Gly
        370                 375                 380

Gly Trp Trp Trp His Asp Glu Cys Gly Glu Asn Asn Leu Asn Gly Lys
385                 390                 395                 400

Tyr Asn Lys Pro Arg Ala Lys Ser Lys Pro Glu Arg Arg Arg Gly Leu
                405                 410                 415

Ser Trp Lys Ser Gln Asn Gly Arg Leu Tyr Ser Ile Lys Ser Thr Lys
                420                 425                 430

Met Leu Ile His Pro Thr Asp Ser Glu Ser Phe Glu Ala Ala Ala Asp
                435                 440                 445

Tyr Lys Asp Asp Asp Asp Lys
450                 455

<210> SEQ ID NO 20
<211> LENGTH: 182
<212> TYPE: PRT
<213> ORGANISM: Artificial Sequence
<220> FEATURE:
<223> OTHER INFORMATION: Synthetic Construct

<400> SEQUENCE: 20

```
Gly Pro Gly Arg Ala Ala Pro Met Gly Gly Pro Glu Leu Ala Gln His
1               5                   10                  15

Glu Glu Leu Thr Leu Leu Phe His Gly Thr Leu Gln Leu Gly Gln Ala
            20                  25                  30

Leu Asn Gly Val Tyr Arg Thr Thr Glu Gly Arg Leu Thr Lys Ala Arg
        35                  40                  45

Asn Ser Leu Gly Leu Tyr Gly Arg Thr Ile Glu Leu Leu Gly Gln Glu
    50                  55                  60

Val Ser Arg Gly Arg Asp Ala Ala Gln Glu Leu Arg Ala Ser Leu Leu
65                  70                  75                  80

Glu Thr Gln Met Glu Glu Asp Ile Leu Gln Leu Gln Ala Glu Ala Thr
                85                  90                  95

Ala Glu Val Leu Gly Glu Val Ala Gln Ala Gln Lys Val Leu Arg Asp
            100                 105                 110

Ser Val Gln Arg Leu Glu Val Gln Leu Arg Ser Ala Trp Leu Gly Pro
        115                 120                 125

Ala Tyr Arg Glu Phe Glu Val Leu Lys Ala His Ala Asp Lys Gln Ser
    130                 135                 140

His Ile Leu Trp Ala Leu Thr Gly His Val Gln Arg Gln Arg Arg Glu
145                 150                 155                 160

Met Val Ala Gln Gln His Arg Leu Arg Gln Ile Gln Glu Arg Leu His
                165                 170                 175

Thr Ala Ala Leu Pro Ala
            180
```

<210> SEQ ID NO 21
<211> LENGTH: 220
<212> TYPE: PRT
<213> ORGANISM: Artificial Sequence
<220> FEATURE:
<223> OTHER INFORMATION: Synthetic Construct

<400> SEQUENCE: 21

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Ser Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Met Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met Gln
                85                  90                  95

Arg Ile Glu Phe Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 22
<211> LENGTH: 220
<212> TYPE: PRT
<213> ORGANISM: Artificial Sequence
<220> FEATURE:
<223> OTHER INFORMATION: Synthetic Construct

<400> SEQUENCE: 22

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Ala Asp Gly Asn Thr Tyr Leu Asp Trp Tyr Leu Gln Lys Pro Gly Gln
        35                  40                  45

Ser Pro Gln Leu Leu Ile Tyr Met Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met Gln
                85                  90                  95

Arg Ile Glu Phe Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 23
<211> LENGTH: 220
<212> TYPE: PRT
<213> ORGANISM: Artificial Sequence
<220> FEATURE:
<223> OTHER INFORMATION: Synthetic Construct

<400> SEQUENCE: 23

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

```
Thr Asp Gly Asn Thr Tyr Leu Asp Trp Tyr Leu Gln Lys Pro Gly Gln
            35                  40                  45

Ser Pro Gln Leu Leu Ile Tyr Met Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Ile Tyr Tyr Cys Met Gln
                 85                  90                  95

Arg Ile Glu Phe Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 24
<211> LENGTH: 220
<212> TYPE: PRT
<213> ORGANISM: Artificial Sequence
<220> FEATURE:
<223> OTHER INFORMATION: Synthetic Construct

<400> SEQUENCE: 24

Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Ile Tyr Tyr Cys Met Gln
                 85                  90                  95

Arg Ile Glu Phe Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175
```

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 25
<211> LENGTH: 220
<212> TYPE: PRT
<213> ORGANISM: Artificial Sequence
<220> FEATURE:
<223> OTHER INFORMATION: Synthetic Construct

<400> SEQUENCE: 25

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Met Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met Gln
                85                  90                  95

Arg Ile Gln Phe Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220
```

ANGPTL3/8 COMPLEXES AND METHODS OF USING THE SAME

The disclosure relates generally to biology and medicine, and more particularly it relates to antibodies (Abs) that bind to and thereby neutralize human angiopoietin-like protein (ANGPTL) 3/8 complexes. Such Abs can increase lipoprotein lipase (LPL) activity and thereby lower serum triglycerides (TGs) such that they may be used in treating lipid metabolism-related and glucose metabolism-related diseases and disorders.

ANGPTLs are a family of proteins that regulate a number of physiological and pathophysiological processes. Of particular interest herein, is the role of ANGPTL3 and ANGPTL8 in lipid and glucose metabolism.

Evidence supports the role of ANGPTL3 as a main regulator of lipoprotein metabolism, and it may regulate TG clearance by inhibiting LPL and inhibiting endothelial lipase (EL). See, Chi et al. (2017) *Mol. Metab.* 6:1137-1149. ANGPTL3 deficiency, inactivation, or loss can result in low levels of low-density lipoprotein-cholesterol (LDL-C), high-density lipoprotein-cholesterol (HDL-C) and TGs. ANGPTL3 also may affect insulin sensitivity, thereby playing a role in modulating not only lipid metabolism but also glucose metabolism. See, Robciuc et al. (2013) *Arterioscler. Thromb. Vasc. Biol.* 33:1706-1713. Nucleic acid and amino acid sequences for human ANGPTL3 are known. For example, one nucleic acid sequence can be found in NCBI Reference Sequence No. NM_014495 (SEQ ID NO:1), and one amino acid sequence can be found in NCBI Reference Sequence No. NP_055310 (SEQ ID NO:2).

ANGPTL8 is highly expressed in the liver and adipose tissue and has been reported to inhibit LPL by complexing with and thereby activating ANGPTL3. See, Chi, supra. Human ANGPTL8 appears to be induced by feeding. Nucleic acid and amino acid sequences for human ANGPTL8 are known. For example, one nucleic acid sequence can be found in NCBI Reference Sequence No. NM_018687 (SEQ ID NO:3), and one amino acid sequence can be found in NCBI Reference Sequence No. NP_061157 (SEQ ID NO:4).

ANGPTL3/8 complexes exist, which have one or more ANGPTL3s that are bound to one or more ANGPTL8s. Evidence suggests these complexes more effectively mediate inhibition of LPL when compared to ANGPTL3 or ANGPTL8 alone. Moreover, ANGPTL3/8 complexes may be made in vitro by co-expressing ANGPTL8 and ANGPTL3 in a mammalian expression system. See, Chi, supra.

Abs are known that bind to either ANGPTL3 or ANGPTL8 and that can be used alone or in combination with each other to treat lipid metabolism-related and glucose metabolism-related diseases and disorders. For example, Intl. Patent Application Publication No. WO 2012/174178 discloses a fully human monoclonal Ab and antigen-binding fragments thereof that bind to ANGPTL3 and interfere with its activity. Other therapeutic anti-ANGPTL3 Abs also are known. See, e.g., Intl. Patent Application Publication No. WO 2008/073300 and U.S. Pat. No. 7,935,796. Likewise, Intl. Patent Application Publication No. WO 2017/027316 discloses a fully human monoclonal Ab or antigen-binding fragments thereof that bind to ANGPTL8 and interfere with its activity. Moreover, Intl. Patent Application Publication No. WO 2017/177181 discloses a combined anti-ANGPTL3 Ab and anti-ANGPTL8 Ab therapy.

Unfortunately, existing Abs that bind only to either ANGPTL3 or ANGPTL8 do not fully abrogate the effect of these ANGPTLs and/or ANGPTL3/8 complexes on lipid and/or glucose metabolism. See, e.g., Dewey et al. (2017) *N. Engl. J. Med.* 377:211-221; and Gusarova et al. (2017) *Endocrinology* 158:1252-1259. In view thereof, there is a need for additional Abs, especially anti-ANGPTL3/8 complex Abs, for treating lipid metabolism-related and glucose metabolism-related diseases and disorders, where such Abs have improved pharmacological inhibitory and/or regulatory properties to modulate lipid and/or glucose metabolism.

To address this need, nucleic and amino acid sequences are provided for a modified ANGTPL3/8 complex. Accordingly, nucleic acid sequences encoding one or more of a modified ANGPTL3 and a modified ANGPTL8 (i.e., fusion proteins) are described herein. In some instances, the nucleic acid sequences include a polynucleotide sequence encoding an ANGPTL3 fusion protein having an amino acid sequence of SEQ ID NO:17. In other instances, the nucleic acid sequences include a polynucleotide sequence encoding an ANGPTL8 fusion protein having an amino acid sequence of SEQ ID NO:18. In still other instances, the nucleic acid sequences include a polynucleotide sequence encoding SEQ ID NO:17 and 18.

Additionally, nucleic acid constructs are provided that include a polynucleotide sequence encoding an ANGPTL3 fusion protein as described herein, an ANGPTL8 fusion protein as described herein, or both, where such constructs can be an expression cassette or a vector.

In view of the above, host cells are provided that include therein one or more expression cassettes or vectors as described herein. In some instances, the host cells are eukaryotic cells. In some instances, the polynucleotide sequences for the ANGPTL3 and ANGTPL8 fusion proteins are on separate expression cassettes or vectors, while in other instances they can be on the same expression cassette or vector.

Also, ANGPTL3 fusion proteins are provided that include an amino acid sequence of SEQ ID NO:17 or 19, as well as active variants or fragments thereof. Likewise, ANGPTL8 fusion proteins are provided that include an amino acid sequence of SEQ ID NO:18 or 20, as well as active variants or fragments thereof.

Moreover, functional ANGPTL3/8 complexes are provided, especially human ANGPTL3/8 complexes, where an ANGPTL3 moiety of the complex is a native (full-length or truncated) ANGPTL3 or an ANGPTL3 fusion protein as described herein and where an ANGPTL8 moiety of the complex is an ANGPTL8 fusion protein as described herein. In some instances, the ANGPTL3 fusion protein includes an amino acid sequence of SEQ ID NO:19. Likewise, and in some instances, the ANGPTL8 fusion protein includes an amino acid sequence of SEQ ID NO:20. Moreover, and in some instances, the complexes can have a 1:1 ratio of the ANGPTL3 moiety to the ANGPTL8 moiety. In other instances, the complexes can have ratios other than 1:1, such as 1:2, 1:3, 2:1 or 3:1 ratio of ANGPTL3 moiety to ANGPTL8 moiety, respectively.

Methods also are provided for making recombinant ANGTPL3/8 complexes. The methods can include at least a step of expressing one or more polynucleotide sequences for an ANGPTL3 moiety and an ANGPTL8 moiety as described herein in a host cell such as in a mammalian expression system to obtain ANGPTL3/8 complexes therefrom. In some instances, the ANGPTL3 and ANGPTL8 moieties are provided on separate expression constructs or vectors. In other instances, ANGPTL3 and ANGPTL8 are provided on one expression construct or vector. The methods also can include a step of purifying the resulting ANGPTL3/8 complexes, which may include not only concentrating the ANGPTL3/8 complexes but also removing one or more of the tags, linkers and serum albumin from the ANGPTL3 moiety and/or the ANGPTL8 moiety. The methods also can include a step of concentrating the ANGPTL3/8 complexes before and/or after purifying step.

Second, an Ab to a ANGPTL3/8 complex is provided as well as uses thereof, which includes treating lipid metabolism-related and glucose metabolism-related diseases and disorders by binding to and thereby inhibiting ANGPTL3/8 complex activity.

An effective amount of the anti-ANGPTL3/8 complex Ab described herein, or a pharmaceutically acceptable salt thereof, may be used for increasing LPL activity, lowering TGs, and treating lipid metabolism- and/or glucose metabolism-related diseases or disorders in an individual in need thereof.

The anti-ANGPTL3/8 complex Ab described herein binds soluble ANGPTL3/8 complex, thereby increasing LPL activity and decreasing serum TG levels. Individuals with lower TG levels are at lower risk for cardiovascular disease. Advantageously, the anti-ANGPTL3/8 complex Ab described herein binds only to the ANGPTL3/8 complex and not to ANGPTL3 alone or to ANGPTL8 alone at relevant concentrations. It is believed that the anti-ANGPTL3/8 complex Ab increases catabolism of TG-rich lipoproteins (TRLs), which reduces TGs and/or non-HDL-C, thereby improving dyslipidemia risk factors for atherosclerotic cardiovascular disease (ASCVD) not addressed by current therapies. Moreover, and because the anti-ANGPTL3/8 complex Ab described herein does not bind ANGPTL3 or ANGPTL8 alone, other actions of these ANGPTLs are not inhibited, which can lead to fewer untoward in vivo effects, such as reduced de-repression of EL.

In particular, the anti-ANGPTL3/8 complex Ab is a human anti-ANGPTL3/8 complex Ab. In some instances, the anti-ANGPTL3/8 complex Ab can abrogate, block, inhibit, interfere, neutralize or reduce in vivo activity of the ANGPTL3/8 complex, especially its LPL inhibitory activity. In some instances, the anti-ANGPTL3/8 complex Ab can be full-length or can be only an antigen-binding fragment (e.g., a Fab, F(ab')2 or scFv fragment). Desirable properties of an anti-ANGPTL3/8 complex Ab include TG lowering at low doses of the Ab, that is durable for at least 21 days.

In some instances, the anti-ANGPTL3/8 complex Ab binds human ANGPTL3/8 complex and includes light chain determining regions LCDR1, LCDR2 and LCDR3 and heavy chain determining regions HCDR1, HCDR2 and HCDR3, where LCDR1 has the amino acid sequence RSSQSLLDSDDGNTYLD (SEQ ID NO:11), LCDR2 has the amino acid sequence YMLSYRAS (SEQ ID NO:12) and LCDR3 has the amino acid sequence MQRIEFPLT (SEQ ID NO:13), and where HCDR1 has the amino acid sequence TFSGFSLSISGVGVG (SEQ ID NO:14), HCDR2 has the amino acid sequence LIYRNDDKRYSPSLKS (SEQ ID NO:15) and HCDR3 has the amino acid sequence ARTYSSGWYGNWFDP (SEQ ID NO:16).

Further provided is an Ab including a light chain variable region (LCVR), where the LCVR has the amino acid sequence of SEQ ID NO:9; or an Ab including a heavy chain variable region (HCVR), where the HCVR has the amino acid sequence of SEQ ID NO:10. In some instances, the Ab includes an LCVR with the amino acid sequence of SEQ ID NO:9 and a HCVR with the amino acid sequence of SEQ ID NO:10. In some instances, the Ab includes a light chain (LC) and a heavy chain (HC), where the LC has the amino acid sequence of SEQ ID NO:5 or the HC has the amino acid sequence of SEQ ID NO:6. Alternatively, the Ab includes a light chain (LC) and a heavy chain (HC), where the LC has the amino acid sequence of SEQ ID NO:5 and the HC has the amino acid sequence of SEQ ID NO:6. In certain instances, the Ab is an IgG4 isotype.

In some instances, the anti-ANGPTL3/8 complex Ab can be a variant of the Ab described above, especially a LC variant having a D31S mutation (SEQ ID NO:21), a D33A mutation (SEQ ID NO:22), a D33T mutation (SEQ ID NO:23); a M56T mutation (SEQ ID NO:24), a E99Q mutation (SEQ ID NO:25) or a combination thereof (e.g., D33T and M56T mutations or D33A and M56T mutations), with respect to a LC having an amino acid sequence of SEQ ID NO:5.

Furthermore, an Ab is provided that is produced by cultivating a mammalian cell including a cDNA molecule, where the cDNA molecule encodes polypeptides having the amino acid sequences of SEQ ID NO:5 and 6, under such conditions that the polypeptides are expressed, and recovering the Ab. Alternatively, an Ab is provided that is produced by cultivating a mammalian cell including two cDNA molecules, where a first cDNA molecule encodes a polypeptide having the amino acid sequence of SEQ ID NO:5, and a second cDNA molecule encodes a polypeptide having the amino acid sequence of SEQ ID NO:6, under such conditions that the polypeptides are expressed, and recovering the Ab. In some instances, the anti-ANGPTL3/8 complex Ab can be a variant of the Ab described above, especially a LC variant having a D31S mutation (SEQ ID NO:21), a D33A mutation (SEQ ID NO:22), a D33T mutation (SEQ ID NO:23); a M56T mutation (SEQ ID NO:24), a E99Q mutation (SEQ ID NO:25) or a combination thereof, with respect to a LC having an amino acid sequence of SEQ ID NO:5.

Moreover, an Ab is provided that binds to and neutralizes human ANGPTL3/8 complex in a standard LPL activity assay with an $EC_{50}$ of 0.5 nM or less. Also, an Ab is provided that binds to human ANGPTL3/8 complex with a dissociation constant of less than or equal to $1 \times 10^{-1}$ M. Moreover, an Ab is provided that binds to human ANGPTL3 and human ANGPTL8 with a dissociation constant of greater than $1 \times 10^{-1}$ M. Furthermore, an Ab is provided that binds to human ANGPTL3/8 complex with a signal greater than 3 fold over the non-binding background signal, as measured by single point ELISA assay, but does not bind to human ANGPTL3 alone or human ANGPTL8 alone with a signal greater than 3 fold over the non-binding background signal, as measured by single point ELISA assay. Likewise, an Ab is provided that lowers TGs in vivo by at least 50% when compared to IgG control at a dose of 10 mg/kg at a time point 14 days after dosing.

Third, a pharmaceutical composition is provided that includes the Ab herein or a population of Abs herein and an acceptable carrier, diluent or excipient. Also provided is a mammalian cell including a DNA molecule including a polynucleotide sequence encoding polypeptides having amino acid sequences of SEQ ID NO:5 and SEQ ID NO:6, where the cell is capable of expressing an Ab herein. Further provided is a mammalian cell including a first DNA molecule and a second DNA molecule, where the first DNA molecule includes a polynucleotide sequence encoding a polypeptide having the amino acid sequence of SEQ ID NO:5, and where the second DNA molecule includes a polynucleotide sequence encoding a polypeptide having the amino acid sequence of SEQ ID NO:6, and where the cell is capable of expressing an Ab herein. In some instances, the anti-ANGPTL3/8 complex Ab can be a variant of the Ab described above, especially a LC variant having a D31S mutation (SEQ ID NO:21), a D33A mutation (SEQ ID NO:22), a D33T mutation (SEQ ID NO:23); a M56T mutation (SEQ ID NO:24), a E99Q mutation (SEQ ID NO:25) or a combination thereof, with respect to a LC having an amino acid sequence of SEQ ID NO:5.

Fourth, a process is provided for producing an Ab, where the process includes cultivating a mammalian cell with a DNA molecule having a polynucleotide sequence encoding polypeptides having the amino acid sequences of SEQ ID NO:5 and SEQ ID NO:6, where the cell is capable of expressing the Ab herein under conditions such that the Ab is expressed, and recovering the expressed Ab. In some instances, the polynucleotide sequence encoding the polypeptide having the amino acid sequence of SEQ ID NO:5 can encode a D31S mutation, a D33A mutation, a D33T mutation, a M56T mutation, a E99Q mutation or a combination thereof. Also provided herein is a method of treating ASCVD, chronic kidney disease (CKD), diabetes, hypertriglyceridemia, nonalcoholic steatohepatitis (NASH), obesity, or a combination thereof, where the method includes administering to an individual in need thereof, an effective amount of an Ab herein. Further provided is a method of lowering TGs that includes administering to an individual in need thereof, an effective amount of an Ab herein.

Fifth, an Ab is provided for use in therapy. In particular, the Ab is for use in the treatment of ASCVD, CKD, diabetes, hypertriglyceridemia, NASH, obsesity, or a combination thereof. Also provided is a pharmaceutical composition for use in treating ASCVD, CKD, diabetes, hypertriglyceridemia, NASH, obsesity, or a combination thereof, that includes an effective amount of the an the Ab herein.

The advantages, effects, features and objects other than those set forth above will become more readily apparent when consideration is given to the detailed description below. Such detailed description makes reference to the following drawing(s), where:

FIG. 1 shows an image of a SDS-page gel showing ANGPTL3/8 complex run under reduced and non-reduced conditions.

Reference to an element by the indefinite article "a" or "an" does not exclude the possibility that more than one element is present, unless the context clearly requires that there be one and only one element. The indefinite article "a" or "an" thus usually means "at least one."

Definitions

As used herein, "about" means within a statistically meaningful range of a value or values such as, for example, a stated concentration, length, molecular weight, pH, sequence similarity, time frame, temperature, volume, etc. Such a value or range can be within an order of magnitude typically within 20%, more typically within 10%, and even more typically within 5% of a given value or range. The allowable variation encompassed by "about" will depend upon the particular system under study, and can be readily appreciated by one of skill in the art.

As used herein, "affinity" means a strength of an Ab's binding to an epitope on an ANGPTL3/8 complex.

As used herein, "angiopoietin-like protein 3" or "ANGPTL3" means a protein having an amino acid sequence including SEQ ID NO:2.

As used herein, "angiopoietin-like protein 8" or "ANGPTL8" means a protein having an amino acid sequence including SEQ ID NO:4.

As used herein, "ANGPTL3/8 complex" means a multi-protein complex of one or more ANGPTL3 compounds that are bound to one or more ANGPTL8 compounds.

As used herein, "anti-ANGPTL3/8 complex Ab" or "anti-ANGPTL3/8 complex Ab" means an Ab that simultaneously recognizes and binds to an area on both ANGPTL3 and ANGPTL8, especially when in the form of the ANGPTL3/8 complex. Generally, an anti-ANGPTL3/8 complex Ab will usually not bind to other ANGPTL family members (e.g., ANGPTL1, ANGPTL2, ANGPTL4, ANGPTL5, ANGPTL6 or ANGPTL7). Moreover, and as noted elsewhere, an anti-ANGPTL3/8 complex Ab also will not bind to ANGPTL3 or ANGPTL8 alone at specified concentrations, as described in the single point ELISA assay below.

As used herein, "bind" or "binds" means an ability of a protein to form a type of chemical bond or attractive force with another protein or molecule as determined by common methods known in the art. Binding can be characterized by an equilibrium dissociation constant ($K_D$) of about $1 \times 10^{-6}$ M or less (i.e., a smaller $K_D$ denotes a tighter binding). Methods of determining whether two molecules bind are well known in the art and include, for example, equilibrium dialysis, surface plasmon resonance, and the like. Here, an anti-ANGPTL3/8 complex Ab binds only the ANGPTL3/8 complex and does not bind ANGPTL3 alone or ANGPTL8 alone. Whether an Ab binds only to the ANGPTL3/8 complex and not to ANGPTL3 alone or ANGPTL8 alone can be determined in standard ELISA assays in a single point format, as described below and binding may be characterized by Biacore, as described below. While the Abs herein are human, they may, however, exhibit cross-reactivity to other ANGPTL3/8 complexes from other species, for example, cynomolgus monkey ANGPTL3/8 complex, mouse ANGPTL3/8 complex, or rat ANGPTL3/8 complex.

As used herein, "effective amount" means an amount or dose of a compound or a pharmaceutical composition containing the same, which upon single or multiple dose administration to an individual, will elicit a biological or medical response of or desired therapeutic effect on a tissue, system, animal, mammal or human that is being sought by the researcher, veterinarian, medical doctor or other clinician. In some instances, an effective amount of a compound herein or compositions including the same to an individual in need thereof would result in increasing LPL activity. A dose can include a higher initial loading dose, followed by a lower dose. A dose can be administered in any therapeutically effective interval, such as multiple times a day, once daily, every other day, three times a week, two times a week, one time a week, once every two weeks, once a month, once every two months, etc. A dose constituting an effective amount could be between 0.01 mg/kg and 100 mg/kg.

As used herein, "equilibrium dissociation constant" or "$K_D$" means a quantitative measurement of Ab affinity to a particular antigen interaction, such as affinity of an Ab to ANGPTL3/8 complex, especially a measure of a propensity of an Ab/ANGPTL3/8 complex conjugate to separate reversibly into its component parts. Likewise, and as used herein, "equilibrium association constant" or "$K_a$" means an inverse of KID.

As used herein, "functional" means that and ANGPTL3 fusion protein, ANGPTL8 fusion protein or ANGPTL3/8 complex has biological activity akin to that of a native ANGPTL3, a native ANGPTL8 or a native ANGPTL3/8 complex including, for example, inhibiting LPL or acting as an antigen to which an Ab can be made and directed.

As used herein, "glucose metabolism-related disease or disorder" means diabetes and the like.

As used herein, "lipid metabolism-related disease or disorder" means a condition associated with abnormal lipid metabolism such as dyslipidemia, hyperlipidemia and hyperlipoproteinemia, including hypertriglyceridemia, hypercholesterolemia, chylomicronemia, mixed dyslipidemia (obesity, metabolic syndrome, diabetes, etc.), lipodystrophy and lipoatrophy. The term also encompasses certain cardiovascular diseases such as atherosclerosis and coronary artery disease, acute pancreatitis, NASH, obesity and the like.

As used herein, "half-maximal effective concentration" or "$EC_{50}$" means a concentration of an Ab (typically expressed in molar units (M)) that induces a response halfway between a baseline and a maximum after a predetermined period of time. The $EC_{50}$ described herein is ideally 3.0 nM or less.

As used herein, "nucleic acid construct" or "expression cassette" means a nucleic acid molecule having at least a control sequence operably linked to a coding sequence. In this manner, a control sequence such as a promoter is in operable interaction with nucleic acid sequences encoding at least one polypeptide of interest such as the ANGPTL3 fusion proteins described herein and/or the ANGPTL8 fusion proteins described herein. Such nucleic acid constructs can be in the form of an expression or transfer cassette. A nucleic acid construct can include an oligonucleotide or polynucleotide composed of deoxyribonucleotides, ribonucleotides or combinations thereof having incorporated therein the nucleotide sequences for one or more polypeptides of interest.

As used herein, "operably linked" means that the elements of a nucleic acid construct are configured so as to perform their usual function. Thus, control sequences (i.e., promoters) operably linked to a coding sequence are capable of effecting expression of the coding sequence. The control sequences need not be contiguous with the coding sequence, so long as they function to direct the expression thereof (i.e., maintain proper reading frame). Thus, for example, intervening untranslated, yet transcribed sequences, can be present between a promoter and a coding sequence, and the promoter sequence still can be considered "operably linked" to the coding sequence.

As used herein, "control sequence" or "control sequences" means promoters, polyadenylation signals, transcription and translation termination sequences, upstream regulatory domains, origins of replication, internal ribosome entry sites ("IRES"), enhancers, and the like, which collectively provide for replication, transcription and translation of a coding sequence in a recipient host cell. Not all of these control sequences need always be present so long as the selected coding sequence is capable of being replicated, transcribed and translated in an appropriate host cell.

As used herein, "coding sequence" or "coding sequences" means a nucleic acid sequence that encodes for one or more polypeptides of interest, and is a nucleic acid sequence that is transcribed (in the case of DNA) and translated (in the case of RNA) into a polypeptide in vitro or in vivo when placed under the control of appropriate regulatory sequences. The boundaries of the coding sequence(s) are determined by a start codon at a 5' (amino) terminus and a translation stop codon at a 3' (carboxy) terminus. A coding sequence can include, but is not limited to, viral nucleic acid sequences, cDNA from prokaryotic or eukaryotic mRNA, genomic DNA sequences from prokaryotic or eukaryotic DNA, or even synthetic DNA sequences.

With respect to control and coding sequences, they can be native/analogous to the host cell or each other. Alternatively, the control and coding sequences can be heterologous to host cell or each other.

As used herein, "promoter" means a nucleotide region composed of a nucleic acid regulatory sequence, where the regulatory sequence is derived from a gene or synthetically created and is capable of binding RNA polymerase and initiating transcription of a downstream (3'-direction) coding sequence. A number of promoters can be used in nucleic acid constructs, including a native promoter for one or more polypeptides of interest. Alternatively, promoters can be selected based upon a desired outcome. Such promoters can include, but are not limited to, inducible promoters, repressible promoters and constitutive promoters.

As used herein, "variant" means a polynucleotide or a polypeptide having one or more modifications such as an addition, deletion, insertion and/or substitution of one or more specific nucleic acid or amino acid residues when compared to a reference nucleic acid or amino acid sequence. A variant therefore includes one or more alterations when compared to the reference nucleic acid or amino acid sequence. Here, the anti-ANGPTL3/8 complex Ab can have a LC or HC variation. In particular, the Ab can be a LC variant having a D31S mutation (SEQ ID NO:21), a D33A mutation (SEQ ID NO:22), a D33T mutation (SEQ ID NO:23); a M56T mutation (SEQ ID NO:24) or a E99Q mutation (SEQ ID NO:25) with respect to a LC having an amino acid sequence of SEQ ID NO:5. Likewise, the LC variant can be a combination any two of the above such as, for example, D31S and D33A mutations, D31S and D33T mutations, D31S and M56T mutations, D31S and E99Q mutations, D33A and M56T mutations, D33A and E99Q mutations, D33T and M56T mutations, D33T and E99Q mutations, and M56T and E99Q, again with respect to a LC having an amino acid sequence of SEQ ID NO:5. Moreover, the LC variant can be a combination of any three of the above such as, for example, D31S, D33A and M56T mutations, D31S, D33A and E99Q mutations, D31S, D33T and M56T mutations, D31S, D33T and E99Q mutaitons, D33A, M56T and E99Q mutations, and D33T, M56T and E99Q mutations, again with respect to a LC having an amino acid sequence of SEQ ID NO:5. Furthermore, the LC variant can be a combination of any four of the above such as, for example, D31S, D33A, M56T and E99Q mutations; and D31S, D33T, M56T and E99Q mutations, again with respect to a LC having an amino acid sequence of SEQ ID NO:5.

As used herein, "vector" means a replicon, such as a plasmid, phage or cosmid, to which another nucleic acid sequence, such as an expression cassette, may be attached so as to bring about replication of the attached sequence. A vector is capable of transferring nucleic acid molecules to host cells. Vectors typically include one or a small number of restriction endonuclease recognition sites where a nucleotide sequence of interest can be inserted in a determinable fashion without loss of essential biological function of the vector, as well as a selectable marker that can be used for identifying and selecting host cells transformed with the vector. A vector therefor can be capable of transferring nucleic acid sequences to target cells.

As used herein, "treatment" or "treating" means management and care of an individual having a condition for which anti-ANGPTL3/8 complex Ab administration is indicated for the purpose of combating or alleviating symptoms and complications of those conditions. Treating includes administering a compound or compositions containing a compound herein to such an individual to prevent the onset of symptoms or complications, alleviating the symptoms or complications, or eliminating the disease, condition, or disorder. Treating includes administering a compound or compositions containing a compound herein to an individual in need thereof to result in increasing LPL activity and lowering of TGs. The individual to be treated is an animal, espeically a human being.

As used herein, "patient," "subject" and "individual," are used interchangeably herein, and mean an animal, espeically a human. In certain instances, the individual is a human and is further characterized with a disease, disorder or condition that would benefit from administration of an anti-ANGPTL3/8 complex Ab.

As used herein, "antibody" or "Ab" and the like means a full-length Ab including two heavy chains and two light chains having inter- and intra-chain disulfide bonds. The amino-terminal portion of each of the four polypeptide chains includes a variable region primarily responsible for antigen recognition. Each HC includes an N-terminal HCVR and an HC constant region (HCCR). Each light chain includes a light chain (LC) variable region (LCVR) and a LC constant region (LCCR). Here, the Ab is an immunoglobulin G (IgG) type Ab, and the IgG isotype may be further divided into subclasses (e.g., IgG1, IgG2, IgG3 and IgG4). The HCVR and LCVR regions can be further subdivided into regions of hyper-variability, termed complementarity determining regions (CDRs), interspersed with regions that are more conserved, termed framework regions (FR). Each HCVR and LCVR includes three CDRs and four FRs, arranged from N-terminus to C-terminus in the following order: FR1, CDR1, FR2, CDR2, FR3, CDR3, FR4. Herein, the three CDRs of the HC are referred to as HCDR1, HCDR2 and HCDR3, and the three CDRs of the LC are referred to as LCDR1, LCDR2 and LCDR3. The CDRs contain most of the residues that form specific interactions with an antigen, such as an ANGPTL3/8 complex. Assigning the residues to the various CDRs may be done by algorithms such as, for example, Chothia, Kabat or North. The North CDR definition is based on affinity propagation clustering with a large number of crystal structures (North et al. (2011) *J. Mol. Bio.* 406:228-256). Herein, the CDRs are best defined by the sequences listed in the Sequence Listing, which are based upon a combination of multiple definitions including North.

An isolated DNA encoding a HCVR region can be converted to a full-length heavy chain gene by operably linking the HCVR-encoding DNA to another DNA molecule encoding heavy chain constant regions. Sequences of human, as well as other mammalian, heavy chain constant region genes are known in the art. DNA fragments encompassing these regions can be obtained by, for example, standard PCR amplification.

An isolated DNA encoding a LCVR region may be converted to a full-length light chain gene by operably linking the LCVR-encoding DNA to another DNA molecule encoding a light chain constant region. Sequences of human, as well as other mammalian, light chain constant region genes are known in the art. DNA fragments encompassing these regions can be obtained by standard PCR amplification. The light chain constant region can be a kappa or lambda constant region.

The Abs herein may contain an IgG4-PAA Fc portion. The IgG4-PAA Fc portion has a Ser to Pro mutation at position 231 (S231P), a Phe to Ala mutation at position 237 (F237A), and a Leu to Ala mutation at position 238 (L238A) as numbered by absolute position in SEQ ID NO:6. The S231P mutation is a hinge mutation that prevents half-Ab formation (phenomenon of dynamic exchange of half-molecules in IgG4 Abs). The F237A and L238A mutations further reduce effector function of the already low human IgG4 isotype. It is contemplated, however, that the Abs herein may alternative include a different Fc portion.

To reduce the potential induction of an immune response when dosed in humans, certain amino acids may require back-mutations to match Ab germline sequences.

Pharmaceutical compositions including the compounds herein may be administered parenterally to individuals in need of such treatment. Such individual may have ASCVD or be at high risk for ASCVD. These individuals may have acute coronary syndromes, history of myocardial infarction (MI), stable or unstable angina, coronary or other arterial revascularization, stroke, transient ischemic attack (TIA), thoracic or abdominal aortic aneurysm, or peripheral arterial disease presumed to be of atherosclerotic origin. Individuals at high risk for ASCVD may further have type 2 diabetes (T2D), CKD or familial hypercholesterolemia (FH).

Parenteral administration may be performed by subcutaneous, intramuscular or intravenous injection by means of a syringe, optionally a pen-like syringe, or mechanical driven injector. Alternatively, parenteral administration can be performed by means of an infusion pump. In some instances, pharmaceutical compositions suitable for administration to an individual having a therapeutically effective amount of a compound oherein and one or more pharmaceutically acceptable excipients. Such pharmaceutical compositions may be prepared by any of a variety of techniques using conventional excipients for pharmaceutical products that are well known in the art. See, e.g., Remington, "The Science and Practice of Pharmacy" (D. B. Troy ed., 21$^{st}$ Ed., Lippincott, Williams & Wilkins, 2006).

The compounds herein may be used in simultaneous, separate or sequential combination with one or more additional therapeutic agents useful for modulating LPL activity, treating lipid metabolism-related diseases or disorders, or treating glucose metabolism-related diseases or disorders, including any of the disorders listed above. Non-limiting examples of the additional therapeutic agents that can be combined with the claimed compounds include, but are not limited to, anti-diabetic agents such as insulin or insulin analogs, biguanides, sulfonylureas, thiazolidinediones, dipeptidyl peptidase-4 ("DPP-4") inhibitors, or sodium-dependent glucose transporter (SGLT2) inhibitors; incretin compounds such as glucagon-like-peptide-1 (GLP-1) or GLP-1 analogs, gastric inhibitory polypeptide (GIP) or GIP analogs, oxyntomodulin (OXM) or OXM analogs; aspirin; antiplatelet agents; H2 receptor blockers; proton pump inhibitors; antihypertensives; lipid modifying therapies such as HMG-CoA reductase inhibitors, PCSK9 inhibitors, cholesterol absorption inhibitors, fibrates, niacin, LXR agonists, RXR agonists, ROR agonists, or reverse cholesterol transport modulators; heart failure therapies such as ACE, angiotensin receptor neprilysin inhibitors, ARB, or B adrenergic antagonists; anti-inflammatory therapies; hypertension therapies, atrial fibrillation therapies; neurodegeneration therapies; oncology therapies; therapies for diabetic cardiomyopathy, diabetic retinopathy, diabetic neuropathy, diabetic nephropathy, weight reduction, wound healing; nephropathy therapies; PAD therapies, or combinations of any of the foregoing agents. The anti-ANGPTL3/8 complex Ab and the one or more additional therapeutic agent(s) can be administered either together through the same delivery route and device such as a single pill, capsule, tablet, or injectable formulation; or separately administered either at the same time in separate delivery devices or routes; or administered sequentially.

Preparation and Purification of ANGPTL3/8 Complexes

One aspect of the disclosure is ANGPTL3/8 complexes that can be used to make an Ab that binds to the complex only and do not bind to ANGPTL3 alone or to ANGPTL8 alone. Although anti-ANGPTL3 Abs and anti-ANGPTL8 Abs are known, there is a challenge in synthesizing sufficient quantities of functional ANGPTL3/8 complexes, especially human ANGPTL3/8 complexes, to make anti-ANGPTL3/8 complex Abs. Additionally or alternatively, such ANGPTL3/8 complexes can be used in assays to assess the properties of Abs directed to ANGPTL3, ANGPTL8 and/or ANGPTL3/8 complexes.

In this manner, the disclosure also describes methods of generating ANGPTL8 by making it as either an N- or a C-terminal serum albumin (e.g., human, mouse or rabbit) fusion protein. Functional ANGPTL3/8 complexes then can be made by co-expressing the ANGPTL8 fusion protein with native ANGPTL3 or an ANGPTL3 fusion protein in a mammalian expression system.

As noted above, nucleic and amino acid sequences for native, human ANGPTL3 and native, human ANGPTL8 are known (see, e.g., SEQ ID NOS:1-2 and 3-4, respectively). ANGPTL3 or ANGPTL 8 as described herein, however, are modified (i.e., recombinant/synthetic) and therefor differ from the native sequences by including additional amino acid sequences to improve generating, secreting and/or complexing ANGTPL3 and ANGTPL8.

For example, ANGPTL3 can be modified to include one or more linkers and tags as are known in the art. Here, human ANGPTL3 (SEQ ID NO:2) is modified to include a linker and FLAG-tag such that the ANGPTL3 fusion protein has an amino acid sequence of SEQ ID NO:17. In some instances, the linker can be from about 1 to about 10 amino acids, such as 3 amino acids, especially 3 Ala residues. The linker and FLAG-tag can be placed at the N- or C-terminus of the ANGPTL3 sequence, especially the C-terminus as in SEQ ID NO:17, where residues 1-460 correspond to ANGPTL3, and residues 461-471 correspond to the 3-Ala linker and FLAG-tag.

Likewise, ANGPTL8 can be modified to include one or more linkers and tags in addition to a sequence for serum albumin, especially human serum albumin. Here, human ANGPTL8 (SEQ ID NO:4) is modified to include a linker, an IgG kappa signal peptide, a polyhistidine (His)-tag, mature human serum albumin, a linker and a PreScission® Cleavage Site such that the ANGPTL8 fusion protein has an amino acid sequence of SEQ ID NO:18. In some instances, the linker can be from about 1 to about 10 amino acids, such as a rigid polyproline repeat, especially an Ala-Pro (AP)-10 linker. The signal peptide, His-tag, mature HSA, linker and PreScission® Cleavage Site can placed at the N- or C-terminus of the ANGPTL8 sequence, especially the N-terminus as in SEQ ID NO:18, where residues 1-20 correspond to the IgG kappa signal peptide, residues 21-27 correspond to the His-tag, residues 28-612 correspond to HSA, residues 613-632 correspond to the AP-10 linker, residues 633-643 correspond to the PreScission® Cleavage Site, and residues 644-820 correspond to ANGPTL8.

Methods of constructing nucleic acid constructs to express the ANGPTL3 fusion protein and/or the ANGPTL8 fusion protein as described herein are well known in the art and can be found in, for example, Balbás & Lorence, "Recombinant Gene Expression: Reviews and Protocols" ($2^{nd}$ Ed. Humana Press 2004); Davis et al., "Basic Methods in Molecular Biology" (Elsevier Press 1986); Sambrook & Russell, "Molecular Cloning: A Laboratory Manual" ($3^{rd}$ Ed. Cold Spring Harbor Laboratory Press 2001); Tijssen, "Laboratory Techniques in Biochemistry and Molecular Biology—Hybridization with Nucleic Acid Probes" (Elsevier 1993); and "Current Protocols in Molecular Biology" (Ausubel et al. eds., Greene Publishing and Wiley-Interscience 1995); as well as U.S. Pat. Nos. 6,664,387; 7,060,491; 7,345,216 and 7,494,805. Because ANGPTL8 does not contain any disulfide bonds, mammalian expression systems can be used. Here, HEK293 expression systems or CHO expression systems may be used to generate the ANGPTL3 and/or ANGPTL8 fusion proteins, especially by co-expression.

In addition to expressing the ANGPTL3 fusion protein and/or the ANGPTL8 fusion protein, the methods also can include purifying the resulting fusion proteins based upon the particular tag used for each fusion protein, which are well known in the art. With regard to the ANGPTL3 and ANGTPL8 fusion proteins described herein, purification can result in a number of truncations after removing the tags such that the ANGPTL3 fusion protein has an amino acid sequence of SEQ ID NO:19 (where residues 1-444 correspond to ANGPTL3, and residues 445-455 correspond to the 3-Ala linker and FLAG-tag) and the ANGPTL8 fusion protein has an amino acid sequence of SEQ ID NO:20 (where residues 1-4 correspond to cleavage residues from the PreScission® Cleavage Site, and residues 5-182 correspond to a fragment of ANGPTL8), which readily associate with one another to form functional ANGPTL3/8 complexes.

Preparation and Purification of Antibodies

Anti-ANGPTL3/8 complex Abs may be produced in a mammalian cell expression system using a CHO GSKO cell line. A glutamine synthetase (GS) gene knockout enables tightened selection stringency by eliminating endogenous GS background activity, which can allow survival of low- or non-productive cells under selection conditions. Genes coding for the Ab HC and LC herein may be sub-cloned into individual GS-containing expression plasmids for co-transfection or both chains may be sub-cloned into a single GS-containing expression plasmid. The cDNA sequence encoding the HC or LC is fused in frame with the coding sequence of a signal peptide, which may be the murine kappa leader sequence, to enhance secretion of the desired product into the cell culture medium. The expression is driven by the viral cytomegalovirus (CMV) promoter.

CHO GSKO cells are stably transfected using electroporation and the appropriate amount of recombinant HC and LC expression plasmids, and the transfected cells are maintained in suspension culture, at the adequate cell density. Selection of the transfected cells is accomplished by growth in glutamine-free, 25 µM methionine sulfoximine (MSX)-containing serum-free medium and incubated at 32-37° C. and 5%-7% $CO_2$. Abs are secreted into the media from the CHO cells. The Abs may be purified by Protein A affinity chromatography followed by anion exchange, or hydrophobic interaction chromatography (or other suitable methods), and may utilize size exclusion chromatography for further purification.

Abs from harvested media are captured onto MabSelect SuRe Protein A resin (GE Healthcare). The resin is then briefly washed with a running buffer, such as a phosphate buffered saline (PBS) pH 7.4 or a running buffer containing Tris, to remove non-specifically bound material. Abs are then eluted from the resin with a low pH solution, such as 20 mM acetic acid/5 mM citric acid. Fractions containing ANGPTL3/8 Abs are pooled and may be held at a low pH to inactivate potential viruses. The pH can be increased as needed by adding a base such as 0.1 M Tris pH 8.0.

ANGPTL3/8 Abs may be further purified by hydrophobic interaction chromatography (HIC) using resins such as Phenyl HP (GE Healthcare). Anti-ANGPTL3/8 Abs can be eluted from the HIC column using a sodium sulfate gradient in 20 mM Tris, pH 8.0. The anti-ANGPTL3/8 Abs may be further purified by size exclusion chromatography using a Superdex 200 column (GE Healthcare) with isocratic elution in PBS, pH 7.4.

The compounds described herein are prepared in this manner or in a similar manner that would be readily determined by one of skill in the art.

Mice harbouring human variable light and heavy chain domains are immunized with the ANGPTL3/8 complex described above, and single antigen-specific B cells are isolated by FACS using ANGPTL3/8 (positive) and ANGPTL3 (negative) as markers. Heavy chain and light chain variable region DNA are recovered from single B cells by PCR and cloned into IgG expression vetors. CHO cell supernatants are tested after transfection for binding activity.

EXAMPLES

The following non-limiting examples are offered for purposes of illustration, not limitation.

Example 1

Making ANGPTL3/8 Complexes

ANGPTL3 and ANGPTL8 Expression: nucleotide sequences encoding an amino acid sequence for human ANGPTL3, a linker and a FLAG tag (SEQ ID NO:17) are inserted into a mammalian expression vector containing a CMV promoter. Likewise, nucleotide sequences encoding an amino acid sequence for human ANGTPL8, mouse IgG kappa signal peptide, HIS-tag, mature human serum albumin (HSA)-PreScission® cleavage site (SEQ ID NO:18) are inserted into a mammalian expression vector containing a CMV promoter. Protein expression is through transient co-transfection of both the above-described expression vectors in HEK293F cells cultured in serum-free media. Culture media is harvested 5 days post transfection and is stored at 4° C. for subsequent protein purification.

Protein Purification: protein purification is conducted at 4° C., where 4 L culture media are supplemented with 1 M Tris-HCl (pH 8.0) and 5 M NaCl to a final concentration of 25 mM and 150 mM, respectively. The media are then incubated with 150 ml of Ni-NTA resin (Qiagen) overnight. The resin is packed into a column and is washed with Buffer A (50 mM Tris-HCl, pH 8.0, 0.3 M NaCl). Protein is eluted with 0-300 mM imidazole gradient in Buffer A. Fractions containing HIS-HSA-ANGPTL8/ANGPTL3-Flag are pooled, concentrated and loaded onto a HiLoad® Superdex® 200 Column (GE Healthcare Biosciences), and eluted with Buffer A. Fractions containing HIS-HSA-ANGPTL8/ANGPTL3-Flag again are pooled, concentrated and digested with PreScission® Protease (GE Healthcare Biosciences) to remove HSA from HIS-HSA-ANGPTL8 fusion protein. The PreScission®-digested protein sample is loaded onto a HiLoad® Superdex® 200 Column and is eluted with storage buffer (20 mM HEPES, pH8.0, 150 mM NaCl). Fractions containing ANGPTL3/8 complex are pooled and concentrated, with protein concentration determined using the Bradford method. ANGTPL3/8 complex is aliquoted and stored at −80° C. until further use.

LPL Activity Assay: An EnzCheck® LPL assay is performed according to the manufacture's instructions (ThermoFisher Scientific). Briefly, ANGPTL3 and the ANGPLT3/8 complexes are serially diluted in growth medium and replaced LPL cell medium for 1 hour incubation. EnzCheck® Lipase Substrate (ELS) is then added into LPL-expressing cells and is incubated for 30 minutes. Fluorescence is measured at 482 nm/515 nm (excitation/emission, respectively). The % inhibition of ANGPTL3 and 3/8 on LPL are calculated.

Results:

Table 1 shows the yield of ANGTPL3/8 complex protein at the various stages of purification/concentration.

TABLE 1

| ANGPTL3/8 Complex Protein Yield. | | | |
|---|---|---|---|
| Start (L) | Ni—NTA Resin Yield (mg) | 1$^{st}$ Superdex ® 200 Column Yield (mg) | 2$^{nd}$ Superdex ® 200 Column Yield (mg) |
| 4 | 105 | 47 | 12 |

Likewise, FIG. 1 shows a 4-20% TG TGX Coomassie-stained gel of the purified and concentrated ANGPTL3/8 complex resulting from the columns, which confirms that complexes form/assemble. Following purification and concentration, ANGTL3 has an amino acid sequence of SEQ ID NO:19 and ANGPTL8 has an amino acid sequence of SEQ ID NO:20.

In the LPL assay, the $EC_{50}$ of ANGPTL3 is 21.5 nM while that of the $EC_{50}$ of ANGTPL3/8 complex is 0.54 nM, which confirms that the complexes are functional.

Example 2

Assays

Single Point ELISA (SPE) Assay: Ab binding selectivity to either the ANGPTL3/8 complex, free ANGPTL3 or free ANGPTL8 is initially verified using standard ELISA assays in a single point format. Briefly, assay plates are coated with an anti-human Fc Ab at a concentration of 2 µg/ml and subsequently blocked with casein. IgG secreted into supernatants after expression in CHO cells are then captured to the assay plate. Biotinylated antigen is added at a concentration of 25 nM to allow for Ab/antigen binding. Ab/antigen complexes are detected after adding alkaline phosphatase-conjugated neutravidin and alkaline phosphatase substrate, and subsequent measurement of the optical density at 560 nm. Positive binding is determined by a signal greater than 3 fold over the non-binding background signal.

ELISA Assay: Ab binding selectivity to either the ANGPTL3/8 complex, free ANGPTL3 or free ANGPTL8 is verified using standard ELISA assays. Briefly, assay plates are coated with an anti-human Fc Ab at a concentration of 2 µg/ml and subsequently blocked with casein. Ab from CHO supernatants after expression in CHO cells is then captured to the assay plate and results is an Ab concentration of 2 µg/ml. Biotinylated antigen (ANGPTL3, ANGPTL8 or ANGPTL3/8 complex) is added at varying concentrations by serial dilution to allow for Ab/antigen binding. Ab/antigen complexes are detected after the addition of alkaline phosphatase-conjugated neutravidin, and alkaline phosphatase substrate, and subsequent measurement of the optical density at 560 nm.

TABLE 2

Ab Binding Selectivity to ANGPTL3/8 Complex, ANGPTL8 and ANGPTL3 in a SPE Assay.

|      | ANGPTL3/8 Complex Binding | ANGPTL8 Binding | ANGPTL3 Binding |
|------|---------------------------|-----------------|-----------------|
| Ab   | 2.302 (positive)          | 0.087 (negative)| 0.074 (negative)|
| D31S | 0.928                     | 0.072           | 0.058           |
| D33A | 0.898                     | 0.118           | 0.076           |
| D33T | 0.661                     | 0.070           | 0.060           |
| M56T | 0.775                     | 0.085           | 0.060           |
| E99Q | 1.538                     | 0.100           | 0.083           |

TABLE 2-continued

Ab Binding Selectivity to ANGPTL3/8 Complex, ANGPTL8 and ANGPTL3 in a SPE Assay.

|                              | ANGPTL3/8 Complex Binding | ANGPTL8 Binding | ANGPTL3 Binding |
|------------------------------|---------------------------|-----------------|-----------------|
| Average Nonbinding Background Signal | 0.09             | 0.07            | 0.08            |
| 3 × Background               | 0.27                      | 0.21            | 0.24            |

Values are optical density (OD) at 560 nm, and the non-binding background signal across all plates tested on average is reflected in the "Background signal" row. This negative control shows the background signal in the absence of Ab.

In the SPE assay, the Ab having a LC of SEQ ID NO:5 and a HC of SEQ ID NO:6 shows positive binding to the human ANGPTL3/8 complex and negative binding to the human ANGPTL8 and human ANGPTL3. Abs with LC variants having a D31S mutation (SEQ ID NO:21), a D33A mutation (SEQ ID NO:22), a D33T mutation (SEQ ID NO:24), a M56T mutation (SEQ ID NO:24) or a E99Q mutation (SEQ ID NO:25) and a HC of SEQ ID NO:6 likewise show binding to the human ANGPTL3/8 complex and negative binding to human ANGPTL8 and human ANGPTL.

TABLE 3

ELISA Assay of Ab Binding to Various Concentrations of ANGPTL3, ANGPTL8 and ANGPTL3/8 Complex.

| Antigen | hANGPTL8 | | hANGPTL3 | | hANGPTL3/8 complex | |
|---------|----------|---------|----------|---------|--------------------|---------|
| conc. [nM] | Ab | Control | Ab | Control | Ab | Control |
| 100   | 0.072 | 0.076 | 0.081 | 0.091 | 2.705 | 0.063 |
| 33.3  | 0.050 | 0.060 | 0.052 | 0.063 | 2.411 | 0.056 |
| 11.1  | 0.045 | 0.051 | 0.046 | 0.052 | 1.708 | 0.047 |
| 3.70  | 0.051 | 0.048 | 0.046 | 0.052 | 1.042 | 0.046 |
| 1.23  | 0.043 | 0.048 | 0.043 | 0.052 | 0.510 | 0.046 |
| 0.412 | 0.046 | 0.050 | 0.043 | 0.067 | 0.231 | 0.046 |
| 0.137 | 0.047 | 0.053 | 0.048 | 0.055 | 0.110 | 0.044 |
| 0.046 | 0.051 | 0.054 | 0.060 | 0.069 | 0.078 | 0.053 |

Control is buffer and no Ab.

The Ab having a LC of SEQ ID NO:5 and a HC of SEQ ID NO:6 shows positive binding to the human ANGPTL3/8 complex in a concentration-dependent manner and no detectable binding to human ANGPTL8 and human ANGPTL3 up to an antigen concentration of 100 nM in this assay (Table 3).

In addition to the above anti-ANGPTL3/8 complex Ab having a LC of SEQ ID NO:5 and a HC of SEQ ID NO:6, Abs with LC variants having a D31S mutation (SEQ ID NO:21), a D33A mutation (SEQ ID NO:22) or a E99Q mutation (SEQ ID NO:25) and a HC of SEQ ID NO:6 are assayed and likewise show positive binding to the human ANGPTL3/8 complex in a concentration-dependent manner and no detectable binding to human ANGPTL8 and human ANGPTL3 up to an antigen concentration of 100 nM in this assay (Tables 4-6).

TABLE 4

ELISA Assay of D31S Variant Ab Binding to Various Concentrations of ANGPTL3, ANGPTL8 and ANGPTL3/8 Complex.

| Antigen | hANGPTL8 | | hANGPTL3 | | hANGPTL3/8 complex | |
|---------|----------|---------|----------|---------|--------------------|---------|
| conc. [nM] | Ab | Control | Ab | Control | Ab | Control |
| 100  | 0.098 | 0.076 | 0.084 | 0.081 | 2.471 | 0.092 |
| 33.3 | 0.063 | 0.065 | 0.069 | 0.064 | 2.226 | 0.068 |
| 11.1 | 0.062 | 0.059 | 0.062 | 0.062 | 1.735 | 0.053 |

TABLE 4-continued

ELISA Assay of D31S Variant Ab Binding to Various Concentrations of ANGPTL3, ANGPTL8 and ANGPTL3/8 Complex.

| Antigen conc. [nM] | hANGPTL8 Ab | Control | hANGPTL3 Ab | Control | hANGPTL3/8 complex Ab | Control |
|---|---|---|---|---|---|---|
| 3.70  | 0.056 | 0.055 | 0.060 | 0.057 | 1.134 | 0.049 |
| 1.23  | 0.058 | 0.049 | 0.059 | 0.058 | 0.575 | 0.048 |
| 0.412 | 0.062 | 0.049 | 0.058 | 0.057 | 0.234 | 0.047 |
| 0.137 | 0.080 | 0.077 | 0.057 | 0.076 | 0.137 | 0.068 |
| 0.046 | 0.096 | 0.085 | 0.060 | 0.064 | 0.149 | 0.075 |

TABLE 5

ELISA Assay of D33A Variant Ab Binding to Various Concentrations of ANGPTL3, ANGPTL8 and ANGPTL3/8 Complex.

| Antigen conc. [nM] | hANGPTL8 Ab | Control | hANGPTL3 Ab | Control | hANGPTL3/8 complex Ab | Control |
|---|---|---|---|---|---|---|
| 100   | 0.078 | 0.076 | 0.082 | 0.081 | 2.388 | 0.092 |
| 33.3  | 0.049 | 0.065 | 0.067 | 0.064 | 2.179 | 0.068 |
| 11.1  | 0.048 | 0.059 | 0.060 | 0.062 | 1.635 | 0.053 |
| 3.70  | 0.048 | 0.055 | 0.056 | 0.057 | 1.040 | 0.049 |
| 1.23  | 0.049 | 0.049 | 0.057 | 0.058 | 0.491 | 0.048 |
| 0.412 | 0.047 | 0.049 | 0.056 | 0.057 | 0.196 | 0.047 |
| 0.137 | 0.053 | 0.077 | 0.062 | 0.076 | 0.101 | 0.068 |
| 0.046 | 0.074 | 0.085 | 0.062 | 0.064 | 0.111 | 0.075 |

TABLE 6

ELISA Assay of E99Q Variant Ab Binding to Various Concentrations of ANGPTL3, ANGPTL8, and ANGPTL3/8 Complex.

| Antigen conc. [nM] | hANGPTL8 Ab | Control | hANGPTL3 Ab | Control | hANGPTL3/8 complex Ab | Control |
|---|---|---|---|---|---|---|
| 100   | 0.098 | 0.076 | 0.084 | 0.081 | 2.471 | 0.092 |
| 33.3  | 0.063 | 0.065 | 0.069 | 0.064 | 2.226 | 0.068 |
| 11.1  | 0.062 | 0.059 | 0.062 | 0.062 | 1.735 | 0.053 |
| 3.70  | 0.056 | 0.055 | 0.060 | 0.057 | 1.134 | 0.049 |
| 1.23  | 0.058 | 0.049 | 0.059 | 0.058 | 0.575 | 0.048 |
| 0.412 | 0.062 | 0.049 | 0.058 | 0.057 | 0.234 | 0.047 |
| 0.137 | 0.080 | 0.077 | 0.057 | 0.076 | 0.137 | 0.068 |
| 0.046 | 0.096 | 0.085 | 0.060 | 0.064 | 0.149 | 0.075 |

Example 3

In Vitro Receptor Affinity

Binding kinetics may be determined using a Biacore® T200 Instrument (GE Healthcare Bio-Sciences Corp.; Piscataway, N.J.). A CM4 sensor chip surface may be prepared by covalent coupling of Human Fab Binder (GE Healthcare Bio-Sciences Corp.). Kinetic experiments may be carried out at about 25° C. in a running buffer of HBSEP+, 0.01% BSA at pH 7.4. Abs may be captured, and a concentration series of mouse, cyno, or human ANGPTL3/8 complex may be injected over the chip surface at about 50 uL/min for about 240 seconds with a dissociation time of about 800 seconds. To determine kinetic parameters (e.g., $k_a$, $k_d$, $K_D$) data is double-referenced and fit to a 1:1 binding model using Biacore T200 Evaluation Software (GE Healthcare Bio-Sciences Corp.). Table 7, below, shows the binding of an anti-ANGPTL3/8 complex Ab having a LC of SEQ ID NO:5 and a HC of SEQ ID NO:6 to various ANGPTL3/8 complexes from different species at pH 7.4 and temperature 25° C.

TABLE 7

Binding of Ab to Cross Species ANGPTL3/8 Complexes at pH 7.4 and Temperature 25° C.

| Species ANGPTL3/8 Complex Binding to Ab | $k_a$ (1/Ms) | $k_d$ (1/s) | $K_D$ (M) | s.d. | N |
|---|---|---|---|---|---|
| Mouse | $4.75 \times 10^5$ | $1.72 \times 10^{-4}$ | $3.66 \times 10^{-10}$ | $6.19 \times 10^{-11}$ | 3 |
| Cyno  | $4.91 \times 10^5$ | $9.91 \times 10^{-5}$ | $2.13 \times 10^{-10}$ | $6.30 \times 10^{-11}$ | 3 |
| Human | $4.77 \times 10^5$ | $6.31 \times 10^{-5}$ | $1.35 \times 10^{-10}$ | $2.69 \times 10^{-11}$ | 2 |

In addition to the above anti-ANGPTL3/8 complex Ab having a LC of SEQ ID NO:5 and a HC of SEQ ID NO:6, Abs with LC variants having a D31S mutation (SEQ ID NO:21), a D33A mutation (SEQ ID NO:22) or a E99Q mutation (SEQ ID NO:25) and a HC of SEQ ID NO:6 are assayed for binding to various ANGPTL3/8 complexes from different species at pH 7.4 and temperature 25° C. (Tables 8-10).

TABLE 8

Binding of D31S Variant Ab to Cross Species ANGPTL3/8 Complexes at pH 7.4 and Temperature 25° C.

| Species ANGPTL3/8 Complex Binding to D31S Ab | $k_a$ (1/Ms) | $k_d$ (1/s) | $K_D$ (M) | s.d. | N |
|---|---|---|---|---|---|
| Mouse | $4.96 \times 10^5$ | $1.08 \times 10^{-4}$ | $2.18 \times 10^{-10}$ | $1.88 \times 10^{-11}$ | 3 |
| Cyno | $4.62 \times 10^5$ | $1.68 \times 10^{-4}$ | $3.65 \times 10^{-10}$ | $1.50 \times 10^{-11}$ | 3 |
| Human | $4.97 \times 10^5$ | $5.75 \times 10^{-5}$ | $1.16 \times 10^{-10}$ | $1.91 \times 10^{-11}$ | 3 |

TABLE 9

Binding of D33A Variant Ab to Cross Species ANGPTL3/8 Complexes at pH 7.4 and Temperature 25° C.

| Species ANGPTL3/8 Complex Binding to D33A Ab | $k_a$ (1/Ms) | $k_d$ (1/s) | $K_D$ (M) | s.d. | N |
|---|---|---|---|---|---|
| Mouse | $5.15 \times 10^5$ | $3.47 \times 10^{-4}$ | $6.80 \times 10^{-10}$ | $7.07 \times 10^{-11}$ | 3 |
| Cyno | $4.35 \times 10^5$ | $2.65 \times 10^{-4}$ | $6.09 \times 10^{-10}$ | $1.21 \times 10^{-11}$ | 3 |
| Human | $4.57 \times 10^5$ | $9.19 \times 10^{-5}$ | $2.01 \times 10^{-10}$ | $1.75 \times 10^{-11}$ | 3 |

TABLE 10

Binding of E99Q Variant Ab to Cross Species ANGPTL3/8 Complexes at pH 7.4 and Temperature 25° C.

| Species ANGPTL3/8 Complex Binding to E99Q Ab | $k_a$ (1/Ms) | $k_d$ (1/s) | $K_D$ (M) | s.d. | N |
|---|---|---|---|---|---|
| Mouse | $5.96 \times 10^5$ | $1.51 \times 10^{-4}$ | $2.54 \times 10^{-10}$ | $1.79 \times 10^{-11}$ | 3 |
| Cyno | $6.20 \times 10^5$ | $7.23 \times 10^{-5}$ | $1.16 \times 10^{-10}$ | $8.58 \times 10^{-12}$ | 3 |
| Human | $6.74 \times 10^5$ | $3.26 \times 10^{-5}$ | $4.84 \times 10^{-11}$ | $6.50 \times 10^{-12}$ | 3 |

Example 4

In Vitro Functional Activity LPL Assay

A cell based bioassay is used to assess the ability of the anti-ANGPTL3/8 complex Ab having a LC of SEQ ID NO:5 and a HC of SEQ ID NO:6 to de-repress ANGPTL3/8 purified protein inhibition of LPL activity. The Ab's ANGPTL3/8 inhibitory activity is determined using EnzChek™ Lipase Substrate (ThermoFisher). HEK293 cell lines expressing human, cynomolgus, mouse or rat LPL, and purified human, cynomolgus, mouse or rat ANGPTL3/8 protein. HEK293-LPL generation includes a human embryonic cell line stably expressing human LPL, which is generated (HEK293-huLPL) utilizing standard methods. Briefly, human LPL is cloned into a lentivirus plasmid with a CMV promoter and blasticidin resistance. The plasmid is used to generate a human LPL lentivirus using ViraPower Packaging Mix (Invitrogen). HEK293 cells are incubated with the LPL lentivirus and clones resistant to blasticidin are selected. A clone is chosen after confirming human LPL mRNA expression by qPCR and LPL activity utilizing the EnzChek™ substrate. This process is repeated for cynomolgus, mouse and rat LPL.

Methods are modified from those described in Basu et al. (Basu et al. (2011) *J. Lipid Res.* 52:826-832): (a) HEK293-LPL cells are added to a half area 96-well Poly-D-Lysine coated plate A (human), B (cynomolgus), C (mouse) or D (rat) at a density of 25000 cells/well and are incubated overnight at 37° C., 5% $CO_2$. Ab is serially diluted nine times from a starting stock concentration to generate a ten-point CRC, and then added to purified ANGPTL3/8 proteins (at the $IC_{80}$ concentration of 0.42 nM for human, 0.38 nM for cynomolgus, 0.13 nM for mouse, or 0.81 nM for rat) in 96 well plates E (human), F (cynomolgus), G (mouse) or H (rat).

The media on the HEK293-LPL cells in plates A, B, C, and D are replaced with the ANGPTL3/8 and Ab mixtures from plate E, F, G and H, respectively, and are incubated 1 hr at 37° C., 5% $CO_2$. 10 µl of EnzChek™ Lipase Substrate (prepared at a concentration of 5µM in 0.05% Zwittergent (3-(N,N-Dimethyloctadecylammonio)propanesulfonate) (Sigma) is added to the cells, ANGPTL3/8 and Ab mixture in plates A, B, C and D. A plate reader is used to measure the fluorescence at 482 nm Excitation and 515 nm Emission with a 495 nm cutoff filter. The plates are incubated at 37° C., 5% CO2 in between time points. Relative fluorescence (directly proportional to LPL activity) is calculated by subtracting the signal at 1 min from the signal at 31 min. The efficacy concentration at which the Ab restored LPL activity 50% ($EC_{50}$) is calculated utilizing Excel Fit. The $EC_{50}$ concentrations are shown in Table 11.

The percent derepression is calculated as follows:

$$=(RFU-RFU(MIN))/(RFU(MAX)-RFU(MIN)) \times 100,$$

where MAX=cells alone (LPL) and MIN=cells (LPL)+ANGPTL3/8 CM (conditioned media).

The Ab generally has a low $EC_{50}$ and so is potent in de-repressing LPL. The Ab also has favorable % max de-repression of LPL.

TABLE 11

Ab $EC_{50}$ and % Max Derepression of LPL for Human, Cyno, Mouse and Rat LPL and Human, Cyno, Mouse and Rat ANGPTL3/8 Complex.

| LPL and ANGPTL3/8 Species | Ab $EC_{50}$ (nM) | % Max Derepression of LPL |
|---|---|---|
| human LPL and human ANGPTL3/8 | 0.28 | 102% |
| cyno LPL and cyno ANGPTL3/8 | 1.31 | 96% |
| mouse LPL and mouse ANGPTL3/8 | 1.38 | 103% |
| rat LPL and rat ANGPTL3/8 | 2.77 | 105% |

In addition to the above anti-ANGPTL3/8 complex Ab having a LC of SEQ ID NO:5 and a HC of SEQ ID NO:6, Abs with LC variants having a D31S mutation (SEQ ID NO:21), a D33A mutation (SEQ ID NO:22), a D33T mutation (SEQ ID NO:23) or a E99Q mutation (SEQ ID NO:25) and a HC of SEQ ID NO:6 are assayed to derepress ANGPTL3/8 purified protein inhibition of LPL activity (Table 12).

TABLE 12

Variant Ab EC$_{50}$ and % Max Derepression of LPL for Human and Mouse LPL and Human and Mouse ANGPTL3/8 Complex.

| LPL and ANGPTL3/8 Species | D31S Ab EC$_{50}$ (nM), % Max Derepression LPL | D33A Ab EC$_{50}$ (nM), % Max Derepression LPL | D33T Ab EC$_{50}$ (nM), % Max Derepression LPL | E99Q Ab EC$_{50}$ (nM), % Max Derepression LPL |
|---|---|---|---|---|
| human LPL and human ANGPTL3/8 | 0.86, 106% | 1.14, 103% | 1.56, 105% | 0.49, 106% |
| mouse LPL and mouse ANGPTL3/8 | 1.79, 110% | 4.07, 106% | 4.55, 114% | 1.65, 110% |

Example 5

In Vivo Triglyceride Response

The effect of an anti-ANGPTL3/8 complex Ab having a LC of SEQ ID NO:5 and HC of SEQ ID NO:6 on serum TG is evaluated in mice transgenic for huCETP and huApolipoprotein A1 (a). Blood is collected from the mice, and serum is isolated prior to the start of the experiment. TG is measured in serum samples using a Cobas® clinical chemistry analyzer (Roche). Animals are assigned into 5 groups of 20 to yield groups with similar serum TG averages. Each group of 20 is then further subdivided into 4 groups of 5 with similar serum triglyceride averages. The Ab is administered to mice by a single subcutaneous injection at 1 mg/kg (n=20), 3 mg/kg (n=20), 10 mg/kg (n=20), or 30 mg/kg (n=20) to 4 separate groups of animals. A control antigen binding null isotype matched mAb is administered by a single subcutaneous injection at 30 mg/kg(n=20) to a fifth group of animals.

Blood is collected from the animals 1 hour (n=5), 8 hours (n=5), 1 day (n=5), 2 days (n=5), 3 days (n=5), 7 days (n=5), 14 days (n=5) and 21 days (n=5) after Ab administration. Blood is collected from subgroup A animals at times 1 hour and 3 days. Blood is collected from subgroup B animals at times 8 hours and 7 days. Blood is collected from subgroup C animals at times 1 day and 14 days. Blood is collected from subgroup D animals at times 2 days and 21 days. Serum is prepared from the blood and serum TG levels were measured using a Cobas® clinical chemistry analyzer (Roche). Percent change of TG from the time matched isotype control is calculated for each dose of Ab at each time point. The calculation for percent change is [(Rx Serum triglyceride−time matched isotype control serum triglyceride)/(time matched isotype control serum triglyceride)]× 100. Data is shown in Table 13.

TABLE 13

Percent TG Lowering by Ab Compared to IgG Control of Different Doses of Ab at Different Time Points.

| Time Post Dose | 1 hour | 8 hour | 1 day | 2 day | 3 day | 7 day | 14 day | 21 day |
|---|---|---|---|---|---|---|---|---|
| 1 mg/kg | −22 | −33 | −76* | −66* | −61* | 41 | 6.4 | −20 |
| 3 mg/kg | −26 | −71* | −84* | −77* | −86* | −25 | 19.7 | −19 |
| 10 mg/kg | −27 | −62* | −87* | −89* | −88* | −88* | −64.4* | −28 |
| 30 mg/kg | −23 | −74* | −92* | −87* | −93* | −93* | −89.1* | −75* |

Dunnett's test is used for each data set to compare each treatment group to a time matched control and a p-value of < 0.05 was considered statistically significant.
Groups statistically significant from their time matched controls are designated by a (*) in the table.

The potency of the Ab having a LC of SEQ ID NO:5 and HC of SEQ ID NO:6 at lowering TGs is favorable starting at Day 1 and the favorable effect is sustained until Day 21.

In addition to the above anti-ANGPTL3/8 complex Ab having a LC of SEQ ID NO:5 and a HC of SEQ ID NO:6, Abs with LC variants having a D31S mutation (SEQ ID NO:21), a D33A mutation (SEQ ID NO:22) or a E99Q mutation (SEQ ID NO:25) and a HC of SEQ ID NO:6 are assayed to evaluate change in TGs relative to an IgG control in mice (Table 14).

TABLE 14

Percent TG Lowering Compared to IgG Control of Different Doses of Variant Abs at Different Time Points.

| Time Post Dose | 1 day | 7 day | 15 day | 21 day |
|---|---|---|---|---|
| D31S 3 mg/kg | −83* | −38* | −25 | −12 |
| D31S 10 mg/kg | −90* | −91* | −37* | −21 |
| D33A 3 mg/kg | −74* | −77* | −34* | −10 |
| D33A 10 mg/kg | −78* | −86* | −76* | −60* |
| E99Q 3 mg/kg | −82* | −49* | −5 | 15 |
| E99Q 10 mg/kg | −86* | −91* | −61* | 6 |

Dunnett's test is used for each data set to compare each treatment group to a time matched control and a p-value of <0.05 was considered statistically significant. Groups statistically significant from their time matched controls are designated by a (*) in the table.

The invention claimed is:
1. A polypeptide comprising an amino acid sequence of SEQ ID NO:18 or 20.
2. An angiopoietin-like peptide (ANGPTL)3/8 complex comprising a polypeptide having an amino acid sequence of SEQ ID NO:19 and a polypeptide having an amino acid sequence of SEQ ID NO:20.

* * * * *